US010024985B1

(12) United States Patent
Newman

(10) Patent No.: US 10,024,985 B1
(45) Date of Patent: Jul. 17, 2018

(54) GAMMA RAY DETECTOR WITH TWO-DIMENSIONAL DIRECTIONALITY

(71) Applicant: David Edward Newman, Poway, CA (US)

(72) Inventor: David Edward Newman, Poway, CA (US)

( * ) Notice: Subject to any disclaimer, the term of this patent is extended or adjusted under 35 U.S.C. 154(b) by 0 days.

(21) Appl. No.: 15/807,556

(22) Filed: Nov. 8, 2017

Related U.S. Application Data

(60) Provisional application No. 62/500,474, filed on May 2, 2017, provisional application No. 62/569,581, filed on Oct. 8, 2017, provisional application No. 62/580,960, filed on Nov. 2, 2017.

(51) Int. Cl.
| | |
|---|---|
| *G01V 5/12* | (2006.01) |
| *G01T 1/29* | (2006.01) |
| *G01T 3/06* | (2006.01) |
| *G01V 5/00* | (2006.01) |
| *G01T 1/20* | (2006.01) |
| *G01N 23/04* | (2018.01) |
| *G01T 1/167* | (2006.01) |

(52) U.S. Cl.
CPC .......... *G01T 1/2907* (2013.01); *G01N 23/04* (2013.01); *G01T 1/167* (2013.01); *G01T 1/20* (2013.01); *G01T 3/065* (2013.01); *G01V 5/0016* (2013.01); *G01V 5/0091* (2013.01)

(58) Field of Classification Search
CPC ......... G01T 3/06; G01T 1/243; G01T 1/1642; G01T 3/00; G01T 1/167; G01T 1/20; G01T 1/2907; G01V 5/06; G01V 5/02; G01N 23/09

USPC ...................................................... 250/269.3
See application file for complete search history.

(56) References Cited

U.S. PATENT DOCUMENTS

| | | | |
|---|---|---|---|
| 3,047,721 | A | 9/1959 | Folsom |
| 3,581,090 | A | 5/1971 | Brown |
| 6,100,530 | A | 8/2000 | Kronenberg |
| 6,433,335 | B1 | 8/2002 | Kronenberg |
| 7,026,627 | B2 | 4/2006 | Fowler |
| 7,312,460 | B2 | 12/2007 | Gerl |
| 7,470,909 | B2 | 12/2008 | Larsson |
| 7,595,494 | B2 | 9/2009 | Koltick |
| 7,772,563 | B2 | 8/2010 | LeGoaller |
| 7,994,482 | B2 | 8/2011 | Frank |
| 8,101,919 | B2 | 1/2012 | Madden |
| 8,198,600 | B2 | 6/2012 | Neustadter |

(Continued)

*Primary Examiner* — Taeho Jo

(57) ABSTRACT

The invention is a gamma ray detector that locates a source, both horizontally and vertically. The detector comprises a tubular shield surrounded by scintillator panels. Gammas incident from one side can fully strike the scintillator facing the source, but are blocked from reaching the scintillators on the opposite side of the shield. The scintillator counting rates thus indicate the lateral direction of the source. By iteratively rotating toward the highest-counting scintillator, the detector converges to the source. An additional, central detector can be mounted within the tubular shield. When analyzed with the outer scintillators, the central detector determines the overall angular separation between the source and the detector axis, thereby locating the source in two dimensions automatically. The invention enables rapid detection and precise localization of clandestine nuclear and radiological weapons, despite shielding and clutter obfuscation, while quickly passing clean loads.

20 Claims, 14 Drawing Sheets

(56) References Cited

U.S. PATENT DOCUMENTS

| | | |
|---|---|---|
| 8,247,776 B2 | 8/2012 | Peng |
| 8,299,441 B2 | 10/2012 | Gueorguiev |
| 8,319,188 B2 | 11/2012 | Ramsden |
| 9,190,250 B2 * | 11/2015 | Takeuchi ................ H01J 47/08 |
| 2007/0085014 A1 * | 4/2007 | McIntyre ................ G01T 1/172 |
| | | 250/367 |
| 2007/0152160 A1 * | 7/2007 | Rowland ............. G01V 5/0008 |
| | | 250/363.02 |
| 2007/0221854 A1 * | 9/2007 | Shirakawa ............ G01T 1/169 |
| | | 250/367 |
| 2008/0251728 A1 * | 10/2008 | Madden ................ G01T 1/2008 |
| | | 250/367 |
| 2009/0271143 A1 * | 10/2009 | Shirakawa ............ G01T 1/2018 |
| | | 702/150 |
| 2009/0309032 A1 * | 12/2009 | Ramsden ............. G01T 1/1644 |
| | | 250/370.1 |
| 2010/0046690 A1 * | 2/2010 | Proctor ................ G01V 5/0091 |
| | | 376/154 |
| 2010/0090115 A1 * | 4/2010 | Lerch ...................... G01T 1/161 |
| | | 250/366 |
| 2010/0320390 A1 * | 12/2010 | McKinsey ............. G01T 1/204 |
| | | 250/362 |
| 2011/0303854 A1 | 12/2011 | DeVito |
| 2015/0097122 A1 * | 4/2015 | Nakamura ................ G01T 3/06 |
| | | 250/367 |
| 2016/0306052 A1 | 10/2016 | Ramsden |
| 2017/0261623 A1 * | 9/2017 | Florido ................ G01T 1/2018 |
| 2017/0363768 A1 * | 12/2017 | Berheide ............. G01T 1/2018 |

* cited by examiner

GAMMA RAY DETECTOR WITH TWO-DIMENSIONAL DIRECTIONALITY

CROSS REFERENCES TO RELATED APPLICATIONS

This application claims the benefit of U.S. Provisional Patent Application No. 62/500,474 entitled "Directional Radiation Detector" and filed on May 2, 2017, and U.S. Provisional Patent Application No. 62/569,581 entitled "Gamma Ray Detector with Two-Dimensional Directionality" and filed on Oct. 8, 2017, and U.S. Provisional Patent Application No. 62/580,960 entitled "Gamma Ray Detector with Two-Dimensional Directionality" and filed on Nov. 2, 2017, the entire disclosures of which are incorporated herein by reference.

FIELD OF INVENTION

The invention relates to gamma ray detectors that indicate the direction of a radiation source, and particularly to those that indicate the source direction in two dimensions.

BACKGROUND OF THE INVENTION

Clandestine nuclear weapons are an immediate worldwide threat. Rogue nations with nuclear weapons, or terrorist groups acquiring radiological material, could deliver it to a victim nation via commercial shipping. Advanced radiation detectors are necessary to reveal such weapons among shielding and benign clutter. An urgent national priority is the development of radiation detectors that detect and localize shielded radioactive threats.

Although nuclear and radiological threat materials emit gamma rays, heavy shielding greatly attenuates the signal; consequently they are difficult to detect using current detector technology. Gamma rays are detected when they interact with matter via photoelectric absorption in which the gamma is absorbed and a photoelectron is emitted, or Compton scattering which generates a Compton electron and a scattered gamma ray, or electron-positron pair production. In each case, the energetic electron (or positron) can be detected in a charged-particle detector such as a scintillator, which generates light when traversed by the energetic electrons. Gamma rays are blocked or attenuated most effectively by high-density, high-Z material (Z being the atomic number) such as lead.

In addition to detecting the presence of a threat source, it would be highly advantageous to also determine the location of the source. The location information would greatly improve the reliability of the detection, while greatly reducing false alarms. To be most effective, the detector should locate the source in two dimensions, such as horizontal and vertical directions relative to the detector.

Numerous directional radiation detectors have been proposed. Typically they have one-dimensional directionality, meaning that on a single measurement, they can only indicate whether the source is to the left or right of the detector. Then by analyzing multiple measurements taken at different detector orientations, the prior-art detector may be able to specify the source location in one dimension. This is insufficient for large inspection items such as trucks and railcars and shipping containers that extend in both the horizontal and vertical directions. For these and many other inspection challenges, a one-dimensional localization is not enough. Of course a pair of such prior-art detectors could be used to separately scan horizontally and vertically, but this would require two separate systems and would entail some kind of cumbersome coordination between them. Also the two systems would each have its own background rate, further diluting the threat signature and requiring longer scan times. Alternatively, a single prior-art directional detector could scan horizontally first, then roll by 90 degrees, and then scan vertically; but this would take twice as long and would require a complicated mechanical joint.

Prior art also includes numerous imaging-type gamma cameras which can in principle determine the two-dimensional location of a gamma ray source. Gamma cameras typically employ a collimator (pin-hole, multi-aperture, coded-aperture, or other type collimator), which inevitably results in a large, heavy, expensive system yet has low detection efficiency due to losses in the collimator. Prior art further includes pseudo-imaging gamma systems which are based on measuring or imaging the track of a Compton-scattered electron, or they may detect double-scattering of gammas. In either case, the prior-art systems provide only a very approximate source direction at best, yet are even larger and more complex and less efficient than the collimated gamma cameras. Gamma cameras and the others were developed for medical applications, in which a full gamma ray image is needed so that a physician can determine the distribution of a cancer for example. In contrast, most safety and security applications have no need for a gamma ray image; it is quite sufficient to localize a source, raise an alarm, and trigger a secondary inspection.

An advanced gamma ray detector with two-dimensional directionality would be a huge advantage for safety and security applications, because it would greatly speed up the inspection process, would reveal hidden sources with higher sensitivity, and would enable rapid clearing of clean loads automatically. Even more important, the two-dimensional information would greatly enhance the statistical power of the radiation scan, because even a shielded source would be revealed by gamma rays coming from a particular spot. With prior-art non-directional detectors, it is necessary to detect hundreds or thousands of additional gamma rays above background, just to raise a suspicion that a source is nearby somewhere. With a two-dimensional direction detector, on the other hand, an alarm could be raised after detecting just a few gammas coming from the same location in the cargo. In this way, the two-dimensional localization greatly accelerates the scan and greatly amplifies the reliability of the alarm. In addition, the revealed location would provide a valuable starting point for the secondary inspection team. With such a detector, the entire inspection process could be speeded up, resulting in greatly reduced inspection times and reduced entry waits at shipping ports. And more importantly, it would detect a smuggled weapon.

A two-dimensional directional gamma detector would be enabling for many important applications of radiation detection. Walk-through personnel scanners at nuclear facilities would detect contamination as well as pilfering on the spot. Drive-through vehicle and cargo scanners at shipping ports and border crossings would be greatly improved by such a detector. As a portable survey-type instrument, it would enable faster source localization and simpler operation, with reduced radiation exposure to the inspector. As a mobile scanner, of the type used in wide-area searches for hidden nuclear or radiological weapon materials, it would provide improved sensitivity as well as directionality to the search.

What is needed, then, is an integrated gamma ray detector system with two-dimensional directionality. The detector should indicate, on a single measurement, a direction toward the source, thereby assisting inspectors in finding the source.

Or, even more preferably, the detector would pinpoint the full two-dimensional source location using just a single data acquisition. Preferably such a detector would be compact, fast, highly efficient, capable of high angular precision, and preferably with low cost.

SUMMARY OF THE INVENTION

The invention is a device that detects gamma rays from a radioactive source, and determines a direction toward the gamma ray source. The device indicates whether the source is to the left, right, up, or down relative to the detector axis, as well as intermediate angles. The source can then be located by iteratively rotating the device in the direction indicated. In addition, by interpolating between two measurements at different detector orientations, the device can determine the source direction in two dimensions. Furthermore, with the addition of a central detector having a particular angle-dependent response, the device can calculate the source direction in two dimensions based on a single measurement orientation. In addition, whenever the device is aimed directly at the source, the device recognizes that fact, and indicates that the source has been localized at the current aim point.

An objective of the invention is to provide a two-dimensional directional detector that is high in detection efficiency yet low in weight, and which has sufficient detector area and sensitivity to rapidly detect and localize a gamma ray source with high angular precision.

Before describing the inventive device in further detail, it is advantageous to outline the geometrical relationship between the detector and the source direction. The device uses a spherical coordinate system aligned with the detector axis, and specifies the source direction in terms of an azimuthal angle and a polar angle. The polar angle is the overall angular separation between the detector axis and the source. The azimuthal angle represents a vector pointing toward the source, but projected onto a plane perpendicular to the detector axis. The polar angle is measured from the detector axis, and the azimuthal angle is measured around the detector axis starting at an arbitrary zero-angle. FIG. 2 is a schematic showing the various angles and their relationship graphically.

The inventive detector comprises a tubular shield surrounded by a tubular array of at least four scintillators. As used herein, an item or array is "tubular" if it is hollow and elongate along a symmetry axis. The "detector axis" is the symmetry axis of the shield, which is also the primary axis of the spherical coordinate system. The tubular item also has an "exterior circumferential surface" which is the item's surface that is farthest from the symmetry axis (as opposed to the ends of the tubular item which are orthogonal to the axis, and the interior surface of the hollow item which is nearest to the axis). The tubular item may have a circular cross-section such as a round pipe or annular cylinder; or the tubular item may comprise an array of arcurate segments that are substantially in contact with each other around the detector axis at constant radius; or the tubular item may comprise an array of flat plates that are symmetrically arranged around the detector axis and are substantially in contact with each other.

The array of scintillators "substantially surrounds" the shield if the array of scintillators covers substantially all of the exterior circumferential surface of the shield, but does not cover the ends of the shield which are open. Furthermore, in some embodiments the shield protrudes distally beyond the scintillator array, in which case the scintillator array covers or surrounds the exterior circumferential surface of the shield only aft of the protruding portion of the shield, and does not cover the protruding portion of the shield. More specifically, the scintillator array is bounded distally by a "front face" comprising a plane orthogonal to the detector axis, and the shield may protrude beyond that front face. Typically the protrusion distance is related to the scintillator thickness or to the radius of the shield. In a preferable embodiment, the shield protrusion distance equals at least one scintillator thickness, thereby to prevent any obliquely-arriving gamma rays from triggering the downstream scintillator on the opposite side of the detector axis from the source.

The inventive tubular shield has sufficient radial thickness that the shield "substantially blocks or attenuates gamma rays", which means that the shield prevents at least 50% of incident gamma rays (or their secondaries) from passing therethrough. A thinner shield would not comprise a proper shield for directionality. Any shield that provides less than about 50% attenuation of the gamma rays would not be suitable for this invention due to the low contrast achievable and long integration times required to see any effect. Even more preferably, the shield provides 75% attenuation of the incoming gamma rays, enabling better contrast and shorter acquisition times. Preferably the shield comprises lead or other material with high density and high atomic number since this provides compact attenuation of gammas, although lower atomic number materials such as iron may be used for the shield if sufficiently thick. The hollow tubular shape of the shield results in a substantial reduction in the weight of the shield relative to a solid cylinder of material, while still having sufficient thickness to substantially block or absorb incident gamma rays.

The inventive scintillators comprise flat or arcurate panels of material that emits light when traversed by a charged particle. Suitable scintillators include plastic or polyvinyltoluene "PVT" scintillator, inorganic scintillators, or other scintillating material. The scintillator array may have, for example, eight flat plates arranged octagonally around the detector axis; or the array may comprise 4, 5, 6, 7, or other number greater than three, flat or arcurate plates, arranged to form a generally tubular scintillator array around the detector axis. To maximize the detection efficiency as well as the directional contrast, the scintillators are mounted in close proximity to the exterior circumferential surface of the shield, typically being 0-2 mm from the exterior circumferential surface of the shield and preferably no more than 5 mm from that surface. The scintillators cover that surface with no, or at most minimal, gaps between scintillators, thereby to improve the detection efficiency and sharpen the directionality. Preferably the scintillators are substantially in contact with each other, thereby forming an entire tubular assembly with maximal area coverage and therefore maximal detection efficiency within the available space. Each scintillator may further comprise a "scintillator back-flange" comprising scintillator material affixed to the rearmost region of each scintillator panel and extending radially beyond the exterior surface of the scintillator panel. Preferably both the scintillator panel and the back-flange are viewed by the same light sensor. The purpose of the scintillator back-flange is to provide extra detection area when the detector axis is nearly aligned with the source. In some embodiments, the scintillator panels are quite thin, and therefore would not detect many gammas when viewing the source at very low polar angles. The back-panels solve this by providing additional detection area, thereby ensuring sufficient detection efficiency when the device is nearly aligned with the source.

Each scintillator is typically wrapped in an opaque film such as aluminum foil. Alternatively, each scintillator may be optically decoupled from its neighbors by a thin separator which is opaque and preferably reflecting of the scintillation light. Or, the contacting surfaces of the scintillators may have a reflective layer deposited on the scintillators. Each scintillator in the array is optically coupled to a light sensor that generates an electrical pulse responsive to that light. Suitable sensors include a photomultiplier tube, an avalanche or PIN-junction photodiode, or other light transducer with high sensitivity and low noise.

The inventive device further includes a processor comprising an electronic digital computing device or a logic array. The processor is configured to analyze and compare the scintillator signals, and determine the azimuthal angle toward the gamma ray source. The processor may include analog or digital signal processing means including amplifiers, filters, discriminators, coincidence circuits, and other electronics to enhance detection and reject noise. The processor may include non-transient computer-readable media containing instructions for performing a method to analyze and compare the scintillator signals, and to determine a direction toward the source.

The processor receives the signals from all the scintillators, compares those signals or their corresponding counting rates, and calculates the azimuthal angle of the source, relative to the current detector axis. Here a "counting rate" is the number of scintillator signals exceeding a predetermined threshold, occurring in a particular time interval termed the "integration time". The processor may calculate a "differential" for each scintillator by subtracting the counting rate of the diametrically opposite scintillator, thereby accentuating the contrast between the scintillator facing the source versus the opposite scintillator which is shielded.

The processor accumulates counts from the various scintillators for the integration time and then calculates the azimuthal angle from the accumulated data. Optionally, the integration time may be variable, so that the operator could select a short integration time for a quick initial indication of the source direction, or a longer integration time to obtain a more precise result. Or, the integration time could be adjusted automatically, based on scintillator counting rates for example. In a high-radiation environment with high counting rates, the processor would select a short integration time, thereby obtaining a precise azimuthal angle quickly, and thereby reducing operator exposure in the hazardous environment. If the source is faint or well-shielded, the low counting rates would require a longer integration time to provide a reliable detection.

The azimuthal angle may be derived from the scintillator signals according to an azimuthal angle analysis method, of which examples are provided. In a simplest azimuthal angle analysis method, the azimuthal angle corresponds to the positional angle of the scintillator that has the highest counting rate, since that scintillator is fully exposed to the source while all the others are at least partially shielded from the source. The "positional angle" of a scintillator is the angle of the centroid of that scintillator, measured around the detector axis and starting at the zero-angle. For example the zero-angle may correspond to the centroid of scintillator number 1, which is mounted on the right-hand side of the shield, as viewed from the rear. Then a source located directly above the detector would activate the scintillator on the top surface of the shield, which has a positional angle of 90 degrees around the detector axis, thus corresponding to an azimuthal angle of 90 degrees. Likewise the opposite scintillator, which is located beneath the shield at an angle of 270 degrees, would have the lowest counting rate due to the shielding.

The scintillator signals could be processed by, for example, subtracting a predetermined normal background counting rate for each scintillator, and also may be corrected for the detection efficiency of each scintillator. The azimuthal angle may be determined according to the scintillator that has the highest counting rate, or the largest differential relative to its opposite scintillator. The azimuthal angle may be calculated by interpolating between the two highest-counting (or highest-differential) scintillators. The interpolation is a weighted average of the two scintillator positional angles, according to their respective counting rates (or their differentials). The interpolation would provide a more precise determination of the azimuthal angle.

Optionally, the inventive device may also calculate the polar angle to the source in addition to the azimuthal angle. The azimuthal angle tells the operator what direction to rotate the device, while the polar angle tells the operator how far to rotate it. In a first polar-angle method, the device could interpolate between measurements taken at two orientations that straddle the actual source location. For example, scintillator data may be taken at a first orientation, then rotated according to the calculated azimuthal angle, and further scintillator data are acquired at the new orientation. Preferably the amount of rotation is sufficient that the second orientation overshoots, or appears on the opposite side of, the source than the initial measurement, so that the two measurements straddle the source. Then, the two measurements can be interpolated, and an exact source direction can be calculated by that interpolation. Usually the source is found after just 3 or 4 such steps.

To calculate the polar angle by the interpolation method, the orientation of the detector must be known for the two measurements, typically relating to a ground-based coordinate system. For example the device may include a multi-axis accelerometer and an electronic compass, thereby to determine the orientation of the detector axis in real time as it is rotated and aimed in different directions. Or, if the device is attached to a structure, the device may include angular transducers such as optical angular encoders which measure the pitch and yaw of the detector in real time. Using the orientation data in cooperation with the scintillator data, the two-dimensional direction toward the source can be determined from any two measurements that straddle the source, by interpolation.

The inventive device may be configured to detect when the detector axis is substantially aligned with the source by determining that all of the scintillators have substantially equal counting rates. Preferably the device then activates an indicator indicating that the source is at the detector's aim point, and deactivates the indicator if the device drifts away from the source direction. Optionally, the indicator could be modulated, for example adjusting the indicator's intensity, according to how close the detector axis is to the source direction. If the shield protrudes somewhat beyond the scintillator array, surprisingly high angular precision can be obtained by this "equal-rates" criterion. As used herein, "substantially aligned" means that the detector axis is aimed at the source with sufficiently low uncertainty that the source can be localized among obfuscating clutter. In practice this normally requires an accuracy of about 1 or 2 degrees, and certainly less than 5 degrees of uncertainty. Embodiments of the invention are capable of sub-degree precision. In contrast, prior-art detectors have demonstrated that imprecise localization is of limited usefulness in most inspection applications.

Optionally, an additional central detector may be positioned within the shield. The central detector may comprise PVT or other non-spectroscopic scintillator, or it may be a spectroscopic-type detector such as NaI or HPGe. A "spectroscopic" type detector measures the total energy of the gamma ray and thus helps to identify the isotopic content of the source. In a preferable embodiment, the central detector is substantially recessed relative to the distal end of the shield, thereby tailoring its field of view. Here a "substantial recess" is at least equal to the inner radius of the shield. Such a recessed position ensures that the central detector detects mainly gamma rays from the aim point of the device, rather than backgrounds.

The central detector can also provide a second method for determining the polar angle. To do so, the central detector must be configured so that its angular response is quite different from the angular response of the surrounding scintillators. Then, the signals from the central detector may be correlated with signals from the scintillators to calculate the polar angle at each measurement orientation. Thus the azimuthal direction toward the source may be obtained from the scintillator counting rates alone, while the polar angle may be deduced from the central detector signals correlated with the scintillator signals. The azimuthal and polar angles together thereby fully localize the source direction in two dimensions. Importantly, the source direction is fully determined in two dimensions, directly from the various counting rates, at a single orientation of the detector, and without moving or rotating the detector at all.

Optionally, the inventive processor may be further configured to store information about the detector orientation, the source location, the scintillator signals, the analysis results, and other information related to gamma ray detection or source localization. The invention may include wireless or wired or optical communication means for transmitting and receiving information with another system, including information about the detector position and the detector orientation when the detector axis becomes aligned with the source. The invention may communicate with another similar detector in a local network, or the receiving system may be a central computer that analyzes and archives data from multiple detectors.

Optionally, the inventive device may include an indicator or display that indicates the azimuthal angle of the source relative to the current detector axis. The indicator may comprise a circle of LED's (light emitting diodes) or other luminous components, wherein the particular LED that resides at the azimuthal angle would be illuminated. Additional LED's may be provided to also indicate the size of the polar angle, when determined. Or, the indicator may comprise a flat-screen display that shows an arrow or other rotatable icon, arranged to point parallel to the calculated azimuthal angle, thereby pointing toward the source. In addition, if the processor also calculates the polar angle, the icon may be varied to show the magnitude of the polar angle, for example by showing a longer or brighter or distinctively colored arrow when the polar angle is large or small. Or, the polar angle may be indicated separately from the rotatable icon, using for example a bar widget on the screen, or simply displaying numerical values. The display may also include a special indicator which is activated only when the detector axis is substantially directly aimed at the source, thereby alerting the operator that the detector is pointing directly at the source.

Optionally, the inventive device may include a light beam transmitter, such as a low-power laser pointer or simply a flashlight. The light beam is preferably aligned with the detector axis, thereby illuminating the aim point of the detector. The processor may be configured to vary a property of the light beam according to the polar angle to the source, for example by modulating the light beam in a distinctive way depending on whether the polar angle is large or small. Or, the beam may be configured to indicate the azimuthal angle visually in real time, for example by configuring the beam spot shape to be an asymmetric shape that points in the azimuthal angle direction. Additionally, when the detector axis is substantially aligned with the source, the processor could change the intensity or shape of the beam, or change the color of the beam, or other variation thereby showing the operator that the detector axis is substantially aligned with the source location.

Optionally, the inventive device may include an imaging device, such as a still or video camera, perhaps of the type found on mobile phones and the like. Preferably the camera is aligned with the detector axis, thereby imaging the scene being inspected. Preferably the current aim point of the detector is at the center of the image, or is otherwise indicated on the recorded image. The processor may activate the camera automatically when the processor determines that the detector axis is substantially aligned with the source, or the camera may be configured to collect images continuously, or only upon operator command. Further data, such as the state of the scintillators, or the azimuthal direction indicated by the scintillators, or the calculated polar angle, or other information related to the inspection, may be superposed on the image or otherwise saved along with the image data.

Optionally, cosmic rays and multiscattering events may be excluded by signal processing. For example, any event in which more than one scintillator is triggered at the same time would be rejected. This could also refine the spectrum of a spectroscopy-type central detector, by rejecting events in which any of the scintillators in the outer array has fired simultaneously with the central detector.

The invention provides many advantages over prior-art directional detectors. (a) On a single measurement, the inventive detector provides an azimuthal angle indicating the direction toward the source. (b) The processor may calculate the polar angle of the source by interpolating between two measurements in which the detector orientation is known for each measurement. (c) The processor may also calculate the polar angle by comparing the scintillator signals with a central detector, thereby fully localizing the source after a single measurement. (d) The invention specifically detects when the detector axis is substantially aligned the source, by comparing all the scintillator signals, and thereby determines the source location independently of the other analysis methods. Surprisingly high angular precision is readily obtained. (e) The inventive scintillator array provides high detection efficiency since the scintillators nearly cover the exterior surface of the shield, thereby presenting maximum detection area. This also ensures that the invention can detect gammas from all directions at all times. (f) The device is low in weight, due primarily to making the shield hollow rather than solid, and thereby avoiding excess shield material and weight. (g) The invention is compact, due primarily to placing the scintillators in close proximity to the shield, thereby minimizing the overall envelope of the system, while also enhancing performance. (h) The invention is economical, easy to build, easy to use, and requires no exotic/rare/expensive materials. (i) The invention is suitable for applications as a portable survey instrument, a walk-through portal, a fixed-site cargo and vehicle scanner, or a mobile urban scanner for concealed weapons. (j) By raising an alarm when multiple gammas are detected coming from the same location, the invention effectively counters any attempt to obscure a threat with shielding and obfuscation.

DETAILED DESCRIPTION OF INVENTION

Figure 1:
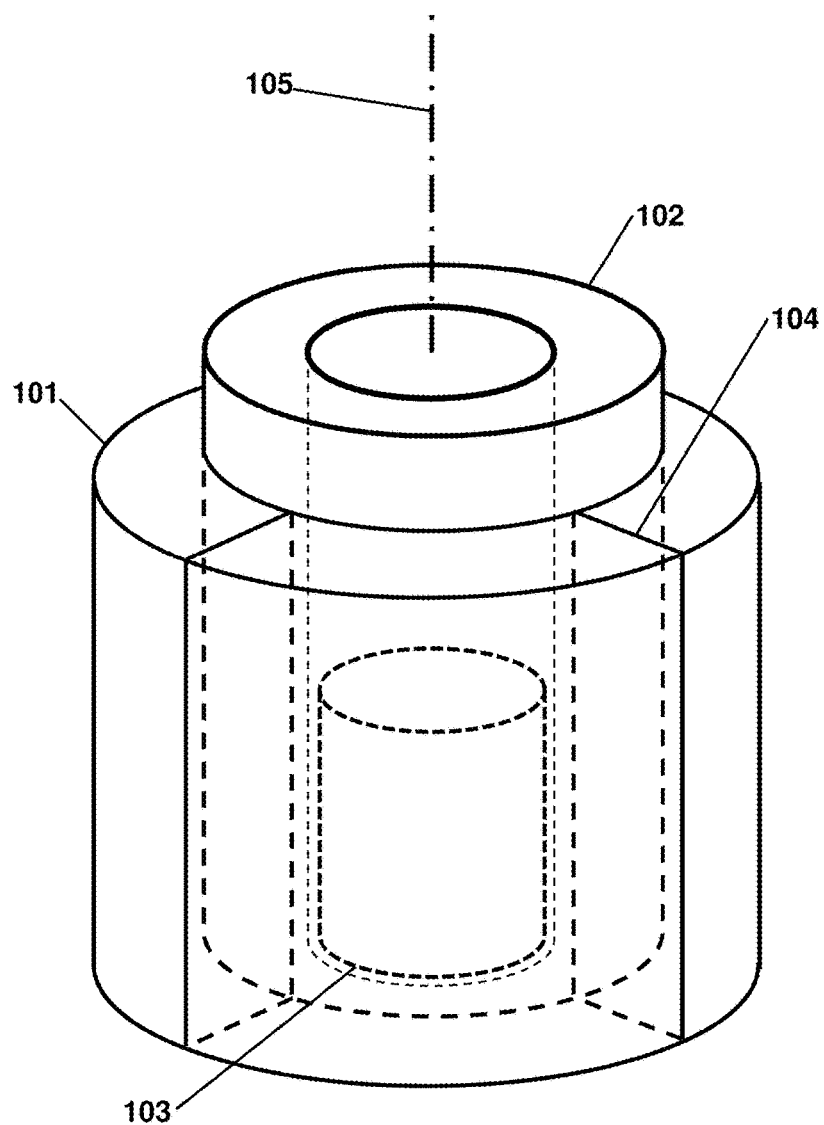
FIG. 1 is a perspective sketch depicting an embodiment of the invention comprising a tubular shield surrounded by a tubular array of scintillators, with an optional central detector inside the shield.

The inventive device is a directional gamma ray detector that determines a direction toward a gamma ray source, relative to the detector axis. By iteratively rotating the detector according to the indicated azimuthal direction, the detector axis is rapidly brought into alignment with the source. The system specifically detects when the detector axis is aligned with the source, and then indicates that the source has been located. The invention may also determine the polar angle to the source by comparing scintillator signals from two different detector orientations. The device may further include a central detector, in which case it may calculate the polar angle of the source by comparing the scintillator signals to the central detector at a single orientation. The invention may average or otherwise combine the polar angle determinations obtained using the interpolation method and central-detector method.

The inventive processor is configured to calculate the azimuthal angle of the source relative to the detector axis based on signals from the array of scintillators that surround the tubular shield. Generally, only one of the scintillators is directly exposed to the source, while the diametrically opposite scintillator is blocked by the shield, and all the other scintillators are only partially exposed if at all. Depending on which scintillator has a high counting rate, the azimuthal angle toward the source is thus revealed. In addition, by interpolating between adjacent scintillators and their respective counting rates, a more precise azimuthal angle can be determined. The detector is then rotated in the direction indicated by the calculated azimuthal angle, and then another measurement is acquired at the new orientation.

The azimuthal angle may be calculated from the scintillator signals, or from the scintillator counting rates, or from the differentials obtained by subtracting from each scintillator counting rate the counting rate of the diametrically opposite scintillator. In each case, the data is accumulated during an integration time, and then reported or indicated. The integration time may be adjusted manually or automatically according to the observed rates. In addition, the device may include means for measuring the orientation of the detector axis relative to a fixed coordinate system, such as true north and horizontal, thereby enabling interpolation between different measurements made at different orientations, and thereby localizing the source. The inventive detector may include an accelerometer and compass to record the detector axis orientation for each scintillator measurement, or a GPS (global positioning system) receiver for determining the detector position, or the detector could include optical angular encoders or the like to track the horizontal and vertical orientation of the detector axis.

As a further option, the device could include a central detector within the shield. Then the polar angle to the source may be calculated by comparing the counting rates of the various scintillators to the central detector. Using data from the central detector, the invention could determine the full two-dimensional direction of the source, using only the data acquired at a single orientation.

The inventive scintillators may have any thickness, so long as they are able to detect gamma rays. The best angular resolution is obtained when the thickness of the scintillator is substantially less than its lateral dimensions; however adequate detection efficiency requires that the scintillators be as thick as possible. Therefore the optimal scintillator thickness is a compromise between angular resolution and detection efficiency. Weight and cost may also be a consideration. The optimal thickness also depends on the material properties of the scintillator, the gamma ray energy, and the shield properties. Good performance can usually be obtained with a plastic scintillator with a thickness in the range of 10-25 mm, or an inorganic scintillator with a thickness of 5-12 mm, although designers may well select larger or smaller thicknesses for specific applications. In addition, a back-flange may be affixed to the rearmost portion of each scintillator, comprising additional scintillator material but with a larger outer radius than the main scintillator panels. The scintillator back-flange provides extra detection area to ensure high detection efficiency when the device is aimed at the source. The scintillator back-flange is particularly important when the scintillator panels are thin, such as BGO with only 5 mm thickness.

The shield may also have any radial thickness, so long as it prevents at least 50% of the incident gamma rays, or their secondaries, from passing through to the scintillators on the opposite side. Preferably the shield is thick enough to attenuate most of the incident gamma rays, but not so thick that the detector becomes too heavy for precise handling. The shield thickness is thus a compromise between weight and signal contrast, where "signal contrast" is the maximum differential between the counting rates of the scintillator facing the source minus the scintillator on the diametrically opposite side. The signal contrast should preferably be at least 2.0 to clearly discern the azimuthal angle; while a contrast of 3.0 would provide much improved responsiveness; and a contrast of 4.0 would be more than ample for most applications. Unlike prior-art collimated detectors, the inventive detector provides rapid convergence and precise angular resolution without the need for a high attenuation factor. Hence there would be little benefit to making the shield a solid body, or any thicker than necessary for a signal contrast of 2 to 4 preferably.

The inventive light sensors may include light guides that convey scintillation light from the scintillators to the light sensors. An advantage of using light guides is that the scintillation light can be collected more uniformly from the entire scintillator area, thereby improving detection efficiency. Another advantage is that the light sensor can be positioned some distance from the scintillators, thereby preventing any extraneous material from getting in the way of the incoming radiation. Another advantage is that accessories such as magnetic shields can usually be accommodated more easily when light guides are used, due to the increased design flexibility.

A first embodiment of the invention comprises a hand-held survey meter, without a central detector. The meter includes a display showing the calculated azimuthal angle of the source, and other data. Operation of the instrument is very simple; the operator rotates the instrument manually, up or down or laterally, according to the indicated azimuthal angle, and thereby converges on the source. The polar angle is not determined and is not necessary in this case, since the operator can find the source simply by following the indicated direction. Normally the operator rotates the instrument slowly, so that it can update the calculated azimuthal angle in real time. If the operator rotates the detector too quickly, the detector axis will likely overshoot the source location; however the system will soon recalculate the azimuthal angle and update the display correctly to point back toward the source. Thus the invention is quite tolerant of operator behavior, quickly and gracefully recovering from overshoot conditions, and thereby reliably guides the operator to the source if one is present. And if there is no source, the system can determine that fact, according to the scintillator rates being about equal to the normal background rates, in which case the system indicates to the operator that there is no source.

A second embodiment comprises a hand-held survey meter which includes means for determining the detector orientation relative to the ground, such as a multi-axis accelerometer and an electronic compass. In that case, the detector orientation is known, and the polar angle is determined by interpolation between two sets of measurements at different detector orientations. Preferably the two orientations straddle the source; however if the two measurements are both on the same side of the source, a rough estimate of the polar angle can still be obtained by projection.

A third embodiment of the invention comprises a hand-held meter or a fixed-site detector, in which a central detector is mounted in the shield. The central detector is configured to have a directional dependence that is quite different from the scintillator array, due to the central detector being in an axially centered position. By analyzing the scintillator signals and the central detector signals together, the polar angle can be calculated at each detector orientation, that is, without the need for correlating successive measurements at different orientations. For example, a ratio Rsc may be calculated, comprising the maximum scintillator counting rate divided by the central detector counting rate. Or, more preferably, the numerator (Rs) equals the maximum differential plus one-half the second-highest differential observed in the scintillator array, while the denominator (Rc) is the central detector counting rate. When calculated with this simple formula, the ratio Rsc=Rs/Rc is closely correlated with the polar angle and is independent of the azimuthal angle.

A fourth embodiment of the invention is a detector mounted in a fixed-site inspection station such as a vehicle inspection station. A large number of detectors could comprise a wall or two walls viewing the vehicle from both sides, or the detectors could be mounted above and below the vehicle, or—even more preferably—as a tunnel that substantially surrounds the vehicle. The detectors can be rotated in both horizontal and vertical directions under computer control according to the azimuthal angle as determined by its scintillator array. Each detector then searches for the source using a predetermined series of rotation steps, such as a binary taper that starts with large rotational angles and proceeds to smaller angular rotations in succeeding measurements. In scanning a newly-presented vehicle, each detector is initially oriented in the center of its range of travel, in both horizontal and vertical dimensions. Then the detector measures the counting rates in the scintillators, and calculates an azimuthal angle from the scintillator data. Then the detector rotates in the direction of the azimuthal angle, and by an amount corresponding to ⅔ of the way to its end of travel. For example, if the range of travel is from −90 to +90 degrees in both horizontal and vertical directions, it would start out at zero degrees for the first acquisition. Then the first rotation corresponds to 60 degrees if the azimuthal angle is horizontal or vertical, or the rotation angle could be as much as 60√2 degrees of rotation if the azimuthal angle is diagonal, thereby corresponding to ⅔ of the maximum travel in that direction. The detector then acquires a second measurement with the new orientation, and re-calculates the azimuthal angle from that perspective. The detector then rotates again, but now by only half as much as the first rotation, and again acquires data. The detector then continues to acquire scintillator data, recalculate the azimuthal angle, and rotate accordingly, but by half as much each time. This procedure ensures that the source will be localized efficiently, assuming that the source is anywhere in the range of travel of the detector. And if the source is outside the range of travel, that fact will be discovered after just two steps. The procedure is efficient because the first measurement divides the possible space into four quadrants and then rotates into the quadrant indicated, and then each successive measurement divides the remaining possible space into four quadrants, and continues likewise until the source is localized.

Alternatively, the detector could be rotated by an amount determined by the data instead of using a predetermined rotation size such as a binary taper. For example, the processor may calculate the polar angle by interpolating between two previous measurements that straddle the source position. Or, the detector may include a central detector, and the processor may calculate the polar angle by comparing the counting rates in the scintillators with the central detector. Or, the processor may employ both the interpolation and the central detector methods in combination, thereby to derive an even more precise prediction of the source location. Then the detector is rotated to that expected source location, according to the azimuthal and polar angles thus determined, and additional data is acquired. After only one or two steps, typically, the detector will have arrived precisely at the source location, which the processor can verify by noting that all the scintillators have about the same counting rate. This procedure leads to the most rapid convergence upon the source location.

As a fifth application embodiment, a large number of the inventive detectors are mounted at a fixed inspection site, and each detector includes a central detector, however the various detectors are mounted in a fixed orientation and are not rotatable. Instead, each detector calculates both azimuthal and polar angles toward the source, and transmits the data to a central computer. The central computer then correlates all of the data from all the detectors, thereby determining (a) whether a source is present or not, (b) its location in three dimensions, and (c) its isotopic composition if the central detectors are spectroscopy type detectors. An advantage of this embodiment is that the expensive angular drive systems and angular readout systems are eliminated. Another advantage is that very high sensitivity can be obtained by use of a large number of detectors aimed all around the vehicle.

The inventive detector may be incorporated in a walk-through portal such as the type used at research laboratories, nuclear reactors, weapon assembly plants, and the like. Radioactive material on a person or carried by the person, either intentionally or unintentionally, would be detected and localized rapidly by the detectors. Preferably detectors are positioned on both sides and overhead and underfoot to scan all parts at once.

The inventive detector may be incorporated in a mobile area scanner. Such a scanner comprises a large number of detectors, mounted inside a truck or similar vehicle, and driven through an area to be searched for hidden nuclear or radiological material. The inventive detector is vastly superior to prior-art non-directional detectors because the inventive detector indicates the location of the source quickly and precisely.

The method may further include displaying the azimuthal angle of the source on a human-readable indicator. The method may include activating an array of luminous items such as at least four, and more preferably eight LED's (light emitting diodes), mounted perhaps in a circular array, with each LED illuminated to indicate the calculated azimuthal angle and optionally the polar angle, when determined. Such an intuitive display would require zero training. After analyzing signals from the various scintillators, and calculating the most probable direction of the source, the processor then illuminates one of the LED's showing how the detector should be rotated to approach the source location. Optionally, to provide a finer directionality, two LED's at different angles may be illuminated simultaneously but with different intensities, thereby suggesting an intermediate angle between the two LED positions. And when there is insufficient data to determine the azimuthal angle, or if no source is present, then all the LED's may be off.

The inventive method may further include activating an indicator when the detector is aimed substantially directly at the source. The processor recognizes such alignment when all of the scintillators in the scintillator array register about the same counting rate, above the normal background rates. The processor may correct for different efficiencies or different background rates of the various scintillators before comparing them. The processor may then indicate that the detector is properly aimed at the source, for example by illuminating all of the LED's simultaneously, or by flashing the LED's characteristically, or by illuminating a special LED which is preferably of a different color than the circle of LED's.

The inventive indicator may comprise a flat-screen display. The method may include presenting a rotatable icon such as an arrow on the display, thereby indicating the azimuthal angle of the source around the detector axis. The polar angle may be calculated, by interpolating previous scintillator data at different detector orientations, or by comparing the counting rates in the scintillators with the central detector, or by other means, and then the rotatable icon may be modulated to indicate how large or small the polar angle is. For example, the length of a rotatable arrow, or its color or intensity, may be adjusted to indicate the magnitude of the polar angle. This would allow the operator to more quickly localize the source by rotating the detector in the right direction (according to the azimuthal angle) and by the right amount (according to the polar angle) to rapidly close in on the source.

A special icon may be shown or flashed when the detector is aimed directly at the source, thereby indicating that the source is at the current aim point of the detector. A neutral icon may be shown when the processor has not yet accumulated sufficient data to calculate the azimuthal angle. If the processor concludes that there is no source present, for example when the scintillators all have counting rates consistent with normal background, then a special icon or message may be shown indicating that. If the device includes a spectroscopic central detector, a gamma ray spectrum may be acquired and shown on the screen, and the radioactive isotope may be identified and also displayed.

As a further option, the processor may calculate the uncertainty in the predicted azimuthal angle, and the indicator may be configured to indicate whether the azimuthal angle is preliminary or high-accuracy. For example, the indicator may be faded or inhibited entirely while the counting rates are low or consistent with background only; and then later, after accumulating more data over a longer integration time, the indicator may be made larger or more intense or otherwise modulated to indicate that the calculated azimuthal angle is more reliable. The directional icon may be modulated as a wide or blunt shape if the uncertainty is large, or as a narrow and sharp icon if the uncertainty is small. If the scintillator counting rates are high, a statistically reliable azimuthal angle may be obtained in a short time, and therefore the indicated direction could be updated quickly, perhaps in near-real-time. But if the source is weak or is far away or is shielded, it may take longer to build up a reliable directional indication. Optionally a separate widget, such as a variable bar or a color-coded patch, may be displayed to indicate the reliability of the angle determination. Such a separate indicator may also provide overall radiation level warnings, so that the operator could escape immediately if the detector indicates that the ambient radiation is hazardous. Also, the counting rate of the central detector may be shown on the display as a bar or other widget, thereby enabling the operator to easily determine when the axis is aligned with the source simply by maximizing the central detector rate.

In some hand-held applications, it may be necessary for the operator to watch the scene constantly, rather than watching the meter. In that case a haptic or acoustical indicator may guide the operator in locating the source. The haptic or acoustical indicator could serve as a simple ratemeter, being activated increasingly according to the radiation level. Or, the haptic or acoustical indicator may be activated only when the counting rate exceeds a threshold. Or, the haptic or acoustical indicator could indicate when the detector axis is substantially pointing toward the source location. Or, a set of haptic panels could be mounted on the detector handle and activated individually, according to the azimuthal angle of the source, so that the operator could determine which way to rotate the detector simply by feel. Acoustical or haptic indicators could enable the operator to locate the source without having to repeatedly look at the screen.

The invention may include a light beam emitter, such as a low-power laser pointer or simply a focused LED or a flashlight, which is preferably aligned with the detector axis. The light beam emitter may be configured to operate continuously, thereby showing the operator exactly where the detector is pointing in real time. Or, the light beam emitter could be activated automatically when the processor determines that the detector axis is substantially aligned with the source. Or, the beam could be turned on or off manually by the operator using a switch. In addition, the device may include two such beams, one being adapted for continuous operation and the other for illuminating only when aligned with the source. The second beam is preferably a different color, or otherwise distinguishable from the first light beam, thereby informing the operator visually that the source has been localized. As a further option, the light beam may be modulated or modified according to the calculated polar angle, for example being larger or redder when the polar angle is large (that is, the detector axis is still far from the source), and progressively finer or bluer as the meter closes in on the source. The operator could easily use this information to rotate the meter by larger or smaller amounts according to the calculated polar angle thus indicated by the light beam.

The light beam could alternatively be configured to indicate the azimuthal direction in real time, thereby visually showing the direction toward the source using the beam spot itself. For example the beam shape could be configured as an arrow or wedge or other asymmetric shape, and configured to point parallel to the azimuthal angle so as to point toward the source. This would greatly assist the operator in scanning the scene to find the source quickly. In a preferred embodiment, the light beam transmitter comprises five separate light beam generators, so as to produce a rotatable beam spot without any moving parts. The first four light sources would produce four overlapping circular beam spots slightly off-axis, forming a cloverleaf pattern, while the fifth light source is much sharper and brighter (such as a laser pointer) and is directed at the center of the cloverleaf. Then, to indicate that the source is to the right, only the left-side illuminator and the central one would be turned on, thereby together forming a wedge-shaped beam spot that clearly points to the right. If the source is upward relative to the current detector axis, the central beam and the lower peripheral beam would be illuminated together, thereby forming an upward-pointing wedge shape. If the source is at an azimuthal angle of 45 degrees, the lower and left peripheral lamps would be illuminated together, along with the central beam, thereby pointing in the diagonal direction. Further angular subdivision can be obtained by varying the intensity of the four outer beams or by providing more peripheral beams, such as eight peripheral beams. Additionally, when the detector axis is aligned with the source, this could be indicated by illuminating all of the beams at once, thereby making a circular bulls-eye-shaped beam spot centered on the source. In addition, if there is insufficient data or no source at all, this could be indicated by illuminating only the central beam spot, with none of the peripheral beams, thereby informing the operator that no source is seen.

The invention determines the azimuthal angle of the source by counting signals from the scintillators for a period of time which is the integration time of the data. After accumulating data for the integration time, the processor applies one of the analysis methods disclosed herein, or other method, to calculate an azimuthal angle from the accumulated data. It may also calculate the polar angle. A short integration time provides quick responsiveness, but the angle determination may be less precise than desired, due to limited statistics obtainable in a short integration time. A long integration time, on the other hand, would provide a more reliable angular determination, but more slowly. If the source is intense enough and the counting rates are high enough, a short integration time is sufficient for an accurate angular determination. If the source is shielded or distant, then a longer integration time is called for.

The inventive device may include a switch so that the operator could select a long integration time or a short integration time or an intermediate integration time depending on circumstances. Or, the integration time could be set automatically by the processor. The integration time could be adjusted inversely according to the scintillator counting rates, with higher rates leading to shorter integration times. Or the integration time may be set dynamically, for example by continuing until a predetermined number of counts have been accumulated. Or the integration time could be continued until a predetermined uncertainty in azimuthal angle has been achieved. As a further option, the system could initially use a short integration time to calculate a preliminary azimuthal angle quickly, and then refine and improve the determination during a longer integration time as further gamma detections are accumulated. The display could be updated as each new determination of the azimuthal angle becomes available, and preferably the operator would be informed in real time as to the current azimuthal angle as well as its uncertainty, by the display. An automatically adjusted integration time would save time and improve directional accuracy, resulting in reduced operator exposure.

The inventive device may include an accelerometer, such as the type found in mobile phones, thereby detecting when the detector is moved or rotated in any direction. Each motion or rotation would preferably cause the processor to dim the directional display, begin the integration time anew, and then prepare an updated directional indication. However, if the detector is rotated sufficiently slowly, as it would be during a careful manual scan, then the system may simply update the previously-acquired data with the newer data as it is acquired. A circular buffer or incremental averaging may be used to successively attenuate the older data as newer measurements arrive. Continuously updating the direction indicator would thus enable the operator to smoothly rotate the detector toward the source direction, using the continuous feedback provided by the device, based on the current azimuthal angle in real time.

The invention may further include an optical imaging device such as a still camera or video camera, preferably aligned with the detector axis, to record images corresponding to the detector field of view. The camera view could also be displayed on a small screen in real time. Such a display could also enable low-light operation if the image sensor (such as a CCD) is sufficiently sensitive. Low-light operation may further be assisted by an infrared illuminator, which may be mounted on the instrument or elsewhere. In addition, the screen display may include magnification, thereby enabling inspecting from a distance. Optionally image enhancement, such as contrast enhancement or color coding, may also be provided. The images may include superposed information about the data, such as the detection rates in the various scintillators and/or the calculated azimuthal angle of the source and/or indications as to whether the detector is aimed directly at the source. Or, the calculated direction of the source, based on the azimuthal and polar angles, may be represented on the image by, for example, a cross-hairs or other icon. The processor could activate the camera to record the scene automatically whenever the processor determines that the various scintillators are all counting at about the same rate, thereby indicating that the detector axis is substantially aligned with the source. Or, the processor could activate the camera whenever the full two-dimensional location of the source has been determined, with an icon superposed at the predicted source location. The detector axis may correspond to the center of the recorded view, or an icon could be superposed on the image at the current aim point, or other indication of the detector axis relative to the image.

The processor may include a wired or wireless or optical or ultrasonic communicator to communicate data such as the orientation of the detector axis, the azimuthal and polar angles as calculated, scintillator rate data, the location of the detector, the radiation level at the detector, whether or not the detector axis is aligned with the source, and the two-dimensional angular direction of a source when localized. The device may include a GPS or other means for determining the location of the detector. That data may be accumulated by a central computer so that multiple detectors acting in cooperation may be analyzed together and the data archived centrally. The data from multiple separate detectors may be combined to enhance detection efficiency, suppress noise, speed the detection cycle, improve sensitivity, and determine the source location in three dimensions by triangulation.

The invention may be embodied as portable or hand-held or autonomous robotic configurations, all of which could include wireless communication for participating in a local network comprising multiple similar detectors. The various detectors in the network could also communicate with a central control station. Often inspectors work in teams, each member circulating in a different route around an inspection zone. If each detector communicates each detector's position, orientation, and scintillator data, then a detailed map of the radiation scene could be accumulated very rapidly. More importantly, the combined data would localize and quantify a threat object without any member having to go near it.

It may be noted that, when the inventive detector is perfectly aligned with a source, the detector cannot tell whether the source is in front or behind the detector, since all of the scintillators in the array would count at the same rate. However this longitudinal ambiguity is easily resolved by rotating the detector a few degrees in any direction and noting which of the scintillators shows an increase in count rate. The sign of this change would be opposite, depending on whether the source is in front or behind the detector. Thus the detector would easily break the longitudinal ambiguity with its first rotation. In practice the longitudinal ambiguity is never an issue, because the detector automatically determines from the first two data points whether the source is in front or behind.

Turning now to the figures, FIG. 1 is a perspective sketch of the inventive detector, including hidden lines in dash. The device is facing upwards in the sketch. The detector comprises a tubular array of scintillators 101 positioned closely around a tubular shield 102 which is coaxial with the scintillator array 101. The symmetry axis of the shield 102 is the detector axis 105. Each scintillator 101 is substantially in contact with its neighbors, but is optically separated from its neighbors by an opaque separator 104. The scintillators 101 thereby form a complete and substantially gapless tubular shape in close proximity to the shield 102. The scintillators 101 are each coupled to a separate light sensor (not shown) which is connected to a processor (not shown). Within the hollow shield 102 is an optional central detector 103, comprising a spectroscopy-type detector that measures the energy of the gamma ray, such as a GeLi or HPGe or NaI detector. The shield 102 protrudes beyond the scintillator array 101 as shown. The scintillator array 101 substantially surrounds the exterior circumferential surface of the shield 102, other than the protrusion area.

Operation of the detector of FIG. 1 is straightforward. Radiation from a source (not shown) is detected primarily in the particular scintillator(s) 101 that directly face the source, while the shield 102 blocks the radiation from reaching the diametrically opposite side. Thus the source direction, relative to the detector axis 105, is apparent in the counting rates of the various scintillators 101. Each scintillator 101 has a positional angle determined by the centroid of that scintillator 101 around the detector axis relative to a zero-angle which is arbitrary. For example the particular scintillator 101 to the right side of the shield 102, as viewed from behind, may have a positional angle of zero degrees, while another scintillator 101 positioned on the top may be at 90 degrees, and so forth. Then the azimuthal angle is equal to the positional angle of the particular scintillator 101 that has the highest counting rate. Alternatively, the azimuthal angle could be based on the largest differential, which is equal to the difference between each scintillator 101 counting rate minus the counting rate of its diametrically opposite counterpart. Or, the azimuthal angle could be calculated by weighted averaging of the highest-counting scintillator 101 with its immediate neighbors, thereby providing finer angular resolution.

After the azimuthal angle is determined, the device is rotated left, right, up, or down, or intermediate angles, according to the azimuthal angle derived from the scintillator 101 counting rates. The device could be rotated slowly enough that the azimuthal angle to the source can be updated in real time, and the device may include accelerometer means to determine whether the rotation is slow enough to permit continuously updating the display. Or, the device could be rotated quickly by an arbitrary amount and then held steady until the azimuthal angle is again determined from the scintillator 101 rates. Iteratively continuing such rotations will bring the detector axis 105 into close alignment with the source.

When the detector axis 105 becomes substantially aligned with the source, all the scintillators 101 would register substantially the same counting rate (net of any differences in sensitivity, which may be previously calibrated and corrected for as needed). Alternatively, all of the differentials become substantially zero. At that orientation, the detector axis 105 thereby identifies the source location as the aim point of the device. In addition, the central detector 103 registers a maximum counting rate when the detector axis 105 is aligned with the source, thereby providing an independent indication of the source location as well as its composition.

The scintillators 101 comprise any material that emits light when traversed by a charged particle such as a Compton electron. An economical choice for the scintillators would be a PVT-based plastic scintillator. Higher detection efficiency can be had by fabricating the scintillators 101 from a dense scintillator material such as CsI, $BaF_2$, LYSO, BGO, NaI, or other scintillators known in the art. The shield 102 may be any dense, preferably $Z \geq 74$, material such as lead, tungsten, or bismuth. It may even be uranium despite its radioactivity. A lower-Z material such as steel may be used if sufficiently thick; however the lowest weight is obtained with a material that has the highest gamma ray attenuation factor, which favors high-Z, high-density materials. Lead was used in the simulations and prototype tests with excellent results.

The sizes of the scintillators 101, and of the shield 102, may be designed according to each particular application. The inner diameter of the scintillator array 101 is typically equal to or slightly larger than the outer diameter of the shield 102. In a preferred embodiment, the outer diameter of the shield 102 may be 90 mm, the radial thickness of the scintillators 101 is 25 mm, and the radial thickness of the shield is 19 mm, and the central detector 103 has an OD of 51 mm. The scintillators 101 may be 75 mm long in the axial direction, while the shield 102 may be 100 mm long. Thus the protrusion of the shield 102 is 25 mm, which is equal to the scintillator thickness.

Figure 2:
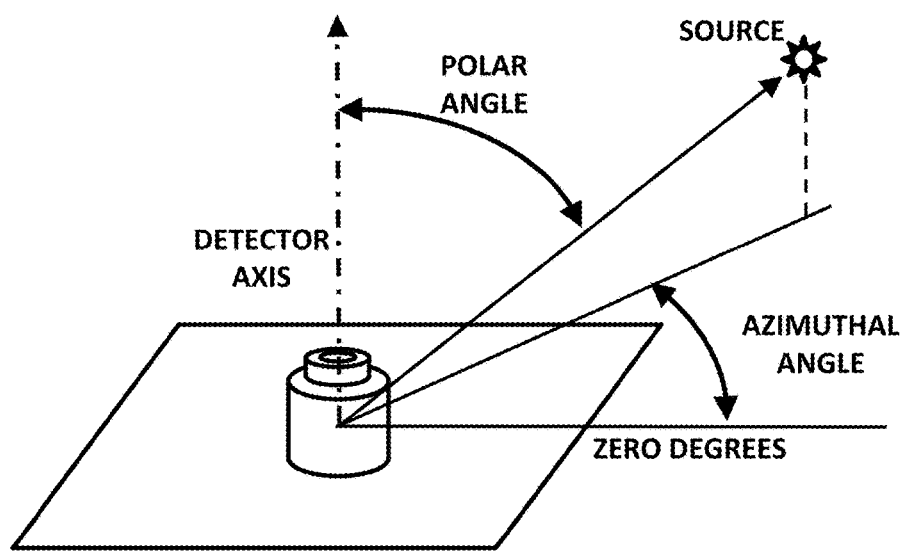
FIG. 2 is a schematic showing in perspective the angles of a spherical coordinate system centered on the detector and aligned with the detector axis. The source direction is then specified by a polar angle relative to the detector axis, and an azimuthal angle measured around the detector axis.

FIG. 2 is a schematic sketch in perspective showing how the azimuthal and polar angles are related to the source location. In a spherical coordinate system aligned with the detector axis, the polar angle of the source is the overall angular separation between the source and the detector axis as shown. The azimuthal angle is the angle of a vector pointing toward the source and projected onto a plane orthogonal to the detector axis. The polar angle ranges from zero to 180 degrees, and is measured relative to the detector axis. The azimuthal angle ranges from zero to 360 degrees, relative to an arbitrary zero angle, which usually corresponds to the center of a particular scintillator of the detector. Thus the azimuthal angle shows in what direction the detector should be rotated to bring it more closely aligned with the source, but does not specify how far to rotate the detector. The polar angle specifies how far the detector should be rotated, but not in what direction. Together, the polar and azimuthal angles fully specify the two-dimensional direction of the source relative to the detector.

Figure 3A:
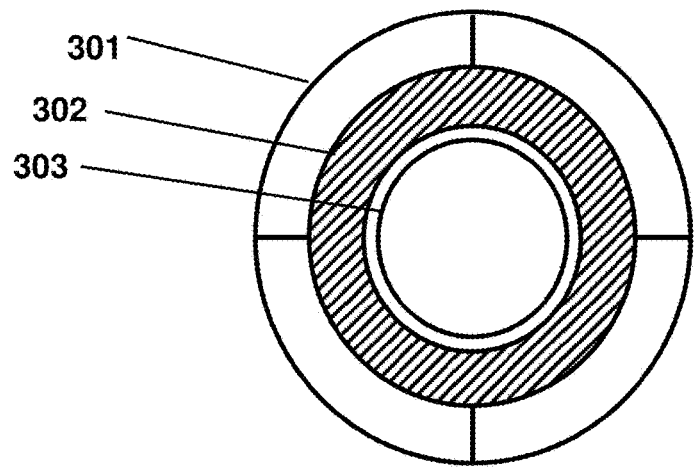
FIG. 3A is a transverse cross-section sketch of the detector of FIG. 1.

FIG. 3A is a cross-section sketch orthogonal to the axis, of a detector such as that of FIG. 1. The arcurate scintillators 301 substantially surround the shield 302 (shown in hatch) which houses the central detector 303. The scintillators 301 are mounted closely proximate to the shield 302 in order to save space, minimize weight, and sharpen the signal contrast.

Figure 3B:
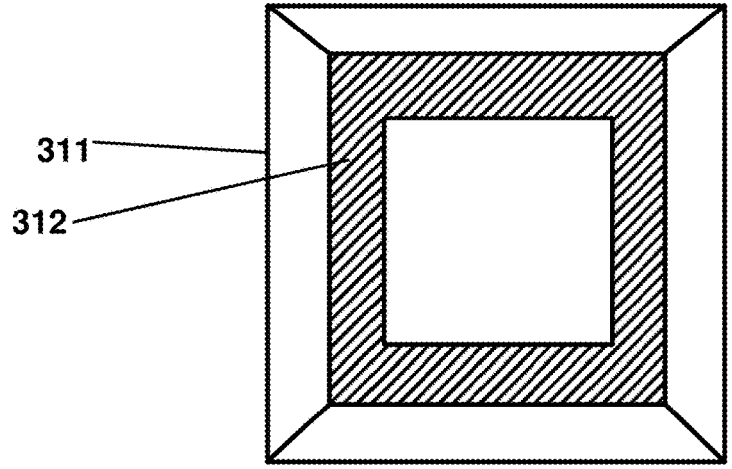
FIG. 3B is a transverse cross-section sketch of the inventive detector with four flat scintillators.

FIG. 3B is a cross-section sketch orthogonal to the axis, of the invention in which four planar scintillators 311 surround a square tubular shield 312. Flat panel scintillators 311 are cheaper, easier to make, and simpler to mount than arc-shaped scintillators. The planar scintillators 311 may have beveled edges as shown, or they may have perpendicular edges for easier fabrication.

Figure 3C:
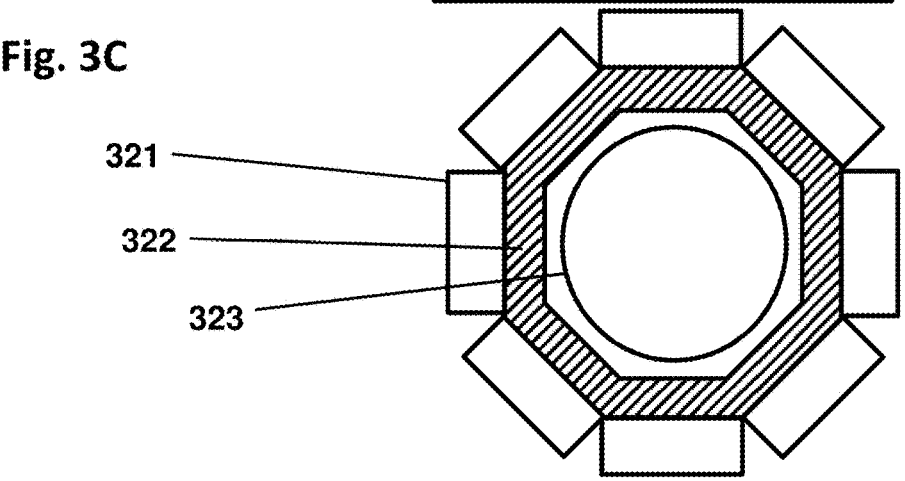
FIG. 3C is a transverse cross-section sketch of the inventive detector with eight scintillators forming an octagonal tube.

FIG. 3C is a cross-section sketch orthogonal to the axis, of an octagonal-tube configuration of the invention, in which eight flat scintillators 321 substantially surround an octagonal-shaped and generally tubular shield 322 which surrounds a central detector 323. The octagonal symmetry provides additional angular resolution as well as redundancy for better sensitivity. Also, the detector may be assembled in sectors if desired, in which each sector comprises one scintillator 321 panel attached to one-eighth of the shield 322. The assembled system then forms a substantially tubular symmetry as shown.

Figure 4:
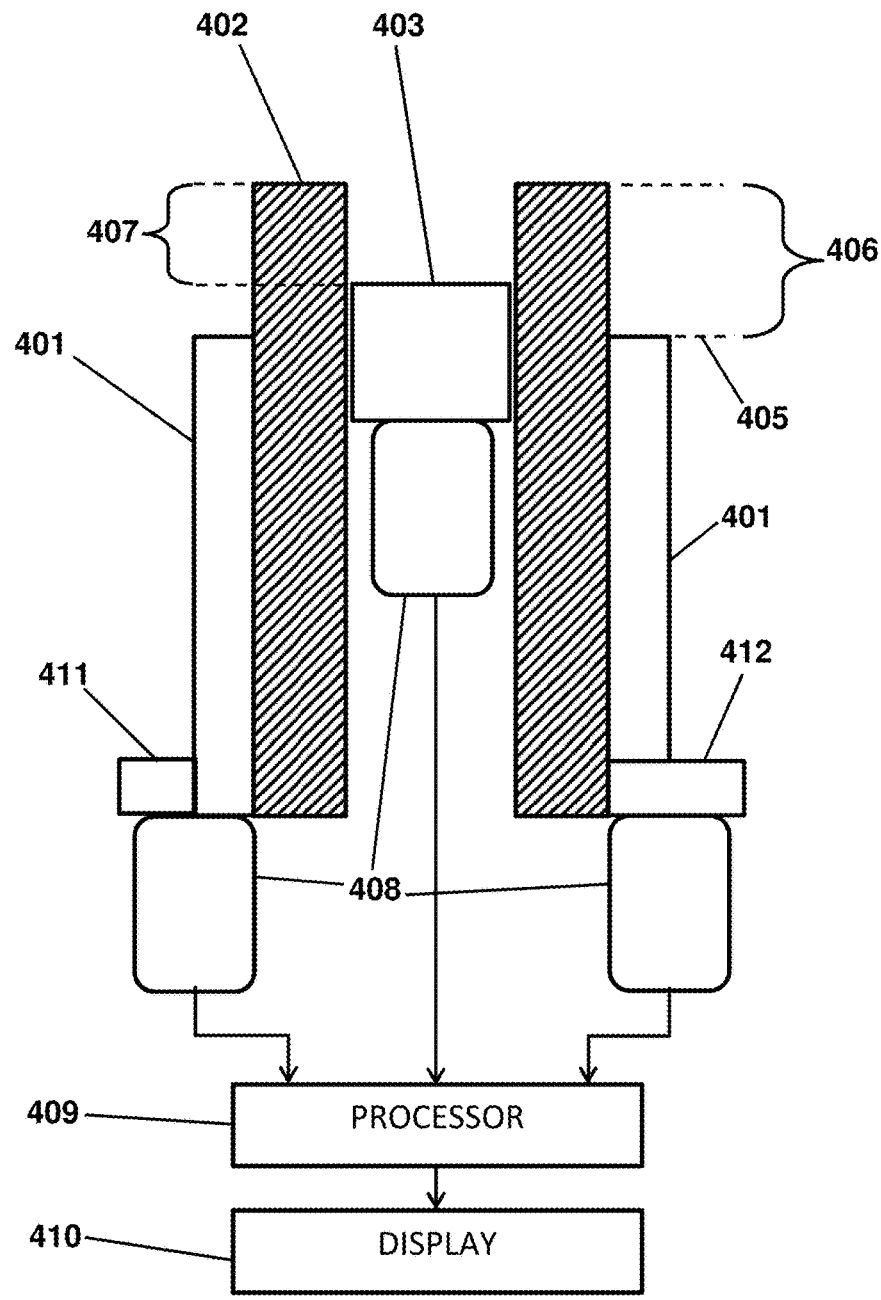
FIG. 4 is a cross-section sketch of the inventive detector, cut parallel to the detector axis. The central detector is positioned for polar angle determination. Further included are light sensors, a processor, and a display.

FIG. 4 is a longitudinal cross-section sketch of the inventive detector such as that of FIG. 1, but now with a light sensor 408 attached to each scintillator 401 and to the central detector 403 which is a NaI detector. The protrusion distance 406 of the shield 402 relative to the scintillators 401 is indicated. Also the central detector 403 is positioned in the shield 402, and recessed from the distal end of the shield 402 by a recess distance 407. When so positioned, the central detector 403 has a polar-angle-dependent detection efficiency which contrasts with that of the scintillators 401. Analyzing signals from the central detector 403 along with the scintillators 401 thereby determines the polar angle of the source. The sketch also shows two versions of the optional scintillator back-flange 411 and 412. In a first version, the back-flange 411 is attached to the rearmost outer surface of the scintillator panel 401, thereby providing extra detection area when gammas arrive essentially parallel to the detector axis. In a second version, the back-flange 412 extends from the rearmost outer surface of the shield 401, and extends radially out past the outer surface of the scintillator 401, thereby again providing additional detection area. Of course the scintillator panel 401 and the back-flange 411 or 412 could be made from a single cast piece rather than in sections as shown.

Output signals from each scintillator 401, and its associated back-flange 411 or 412 when present, and from the optional central detector 403 when present, are routed to a processor 409, which then calculates the azimuthal angle and causes the results to be indicated in a display 410. The processor 409 also combines the data from the scintillators 401 and the central detector 403, for example by calculating a ratio of the counting rates, and thereby calculates the polar angle of the source. Each light sensor 408 is preferably a fast, sensitive phototransducer, such as a photomultiplier tube or an avalanche-type solid-state sensor such as a SiPM. Possibly, several solid-state sensors could be attached to each scintillator 401, and their signals combined to suppress noise. Usually the signals are filtered or amplified or discriminated or otherwise signal-processed by analog or digital electronics. Such electronics may be included in each light sensor 408, or may comprise part of the processor 409, or may be a separate circuit depending on design.

The processor 409 receives the electronic signals from the light sensors 408 and calculates a most probable azimuthal angle for the source, relative to the detector axis. The processor 409 may also correct for differences in efficiency or sensitivity or background rates of each scintillator 401, using previously calibrated measurements with a known source or beam or cosmic rays for example.

The display 410 indicates the azimuthal angle thus calculated, thereby showing which direction the detector should be rotated to more closely align with the source location. The display 410 further indicates the polar angle when known, thereby assisting the operator to rotate the detector by the appropriate amount, and thereby to converge more rapidly on the source direction.

Figure 5A:
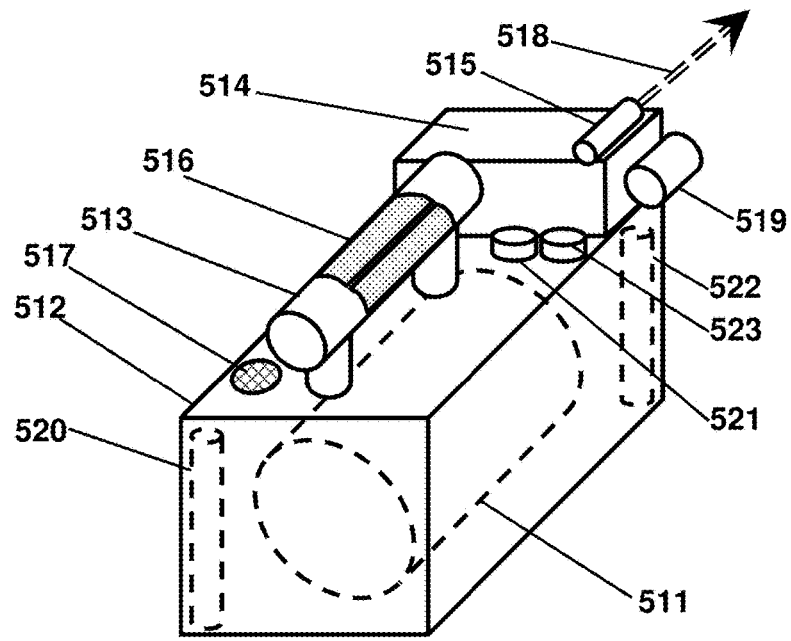
FIG. 5A is a sketch of an embodiment of the invention as a portable survey meter, with numerous accessories.

FIG. 5A is a perspective sketch of a hand-held survey meter incorporating the inventive detector 511 within a case 512 and with a handle 513. Angular results are indicated in a display 514 such as a flat-screen display. Data such as image data and detection data may be stored on-board in a memory (not shown) or transmitted wirelessly by a communicator 520 to another location for analysis and archiving. The system may further be equipped with an electronic compass 522 and accelerometer 523 to indicate the absolute orientation of the detector. When so equipped, the system may then correlate data from multiple measurements at different detector orientations, and thereby apply interpolation, triangulation, weighted averaging and the like to rapidly localize the gamma ray source.

The depicted survey meter further includes multiple haptic panels 516 built into the handle 513. The haptic panels 516 are activated according to the azimuthal angle, and thereby tactually communicate the source direction to the operator. In addition, the haptic panels 516 may also indicate when the detector is aimed directly at the source, for example by pulsing with a characteristic code. The haptic panels 516 could also alert the operator if the local radiation level becomes dangerously high.

The embodiment also includes a small speaker 517 that emits a tone or warble, thereby indicating when the detector axis is substantially aligned with the source. Alternatively the speaker 517 could indicate the direction of the source by various tonal modulations. Or, the speaker 517 could emit computer-generated speech based on the signals detected, such as: "Source is above and to the right of your current aim . . . . A little higher . . . Stop! Source is now localized!"

The survey meter further includes a camera 519 which records the inspection process in video or still photos. The camera 519 could be triggered manually by the operator, or it could be activated automatically upon each azimuthal angle determination, or automatically when the meter becomes aligned with the source.

The configuration further includes a laser pointer 515 which emits a light beam 518 parallel to the detector axis. The light beam 518 visually indicates the current aim point, showing exactly where the meter is pointing at any moment. In addition, the beam 518 may be changed to indicate when the detector is aligned with the source, for example changing the color or intensity or other modulation of the beam 518. Even more preferably, the beam 518 may be varied according to the calculated azimuthal or polar angle, thereby showing the operator how the meter needs to be rotated to reach the source direction.

Figure 5B:
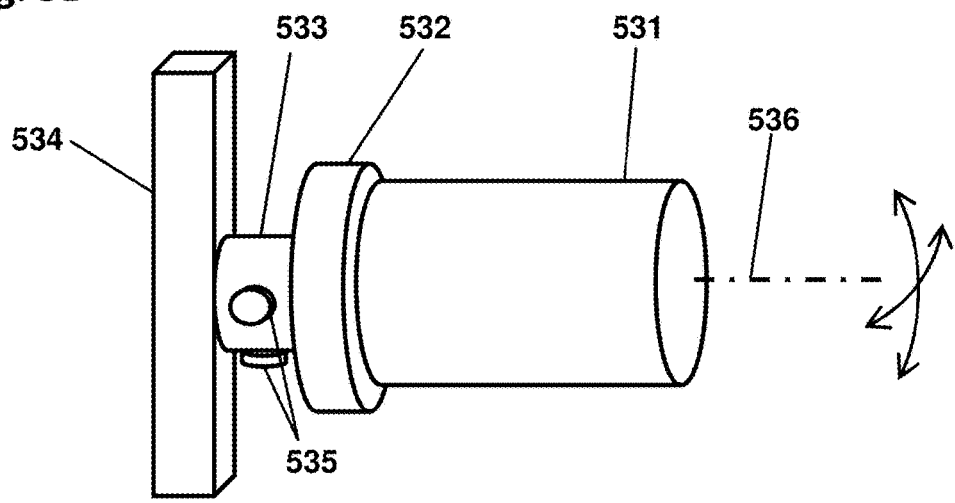
FIG. 5B is a sketch of an embodiment of the invention as a directional detector mounted at an inspection site.

FIG. 5B is a perspective sketch of the inventive detector mounted in an inspection facility, such as a walk-through personnel scanner or an area monitor or a vehicle inspection station for example. The detector 531 is mounted with a rotatable drive 533 and a gimbal or omnidirectional joint 532 mounted to a fixed frame 534. During an inspection, the detector 531 is rotated up and down and sideways as suggested by arrows, thereby iteratively locating a gamma ray source (not shown). The detector orientation, including the vertical and horizontal angles of the detector axis relative to the frame, are measured by two substantially orthogonal angle transducers 535 such as angular optical encoders. The detector angle data, along with detection rates and the like, may be analyzed locally, or may be communicated to a central computer (not shown), which may correlate results from multiple such detectors, thereby localizing a source in three dimensions.

Alternatively, the configuration of FIG. 5B could be mounted along with a large number of similar detectors, but without the rotatable mounts 532 and 533, and without the angular readouts 535, but with a central detector (not shown). Then each such detector could determine an azimuthal angle and a polar angle to the source, while a central computer (not shown) could correlate all of the data to build a three-dimensional model of the inspection vehicle or scene. The advantage of this configuration is low cost, since the expensive mechanicals and angular readouts are eliminated.

Figure 6A:
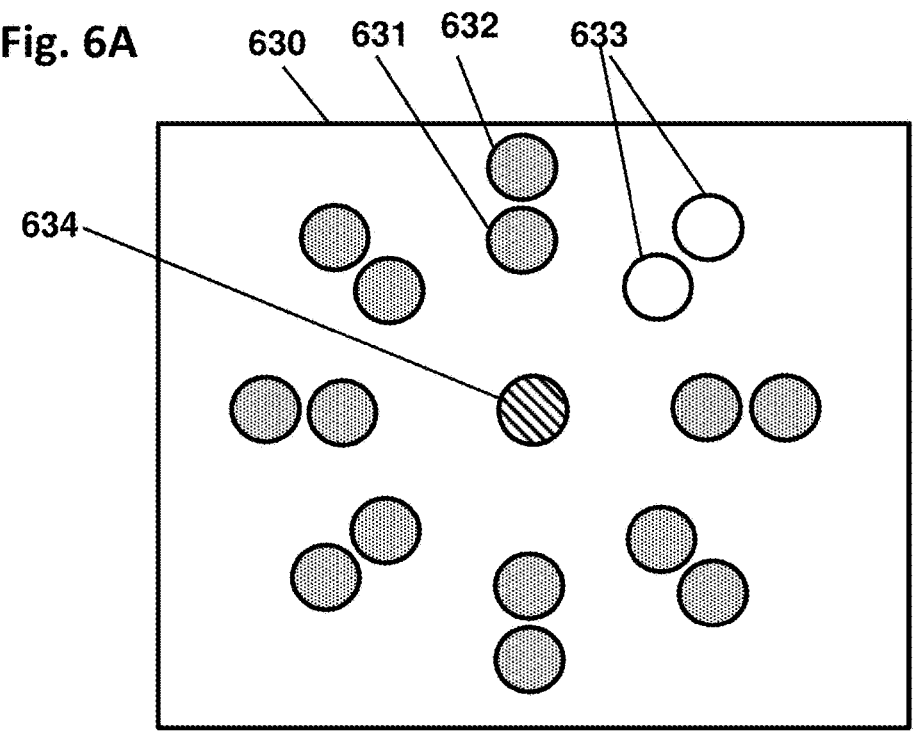
FIG. 6A is a sketch of the inventive direction indicator comprising LED's.

FIG. 6A is a sketch showing a visual display 630 comprising luminous indicators such as LED's. The display 630 includes an inner circle of indicators 631 and an outer circle of indicators 632. The indicators 631 and 632 are configured and powered to show the azimuthal angle of the source around the detector axis, and optionally the polar angle, when determined. The angular position of any illuminated LED's indicates the azimuthal angle of the source. The number of illuminated LED's at each azimuthal angle also indicates the polar angle as being relatively large or small. For example, if the polar angle is small, such as less than 30 degrees for example, then only one LED at a particular angle would be lit, while if the polar angle is greater than 30 degrees, both LED's at the azimuthal angle would be illuminated. In the figure, one pair of LED's 633 in the upper-right are illuminated, thus indicating that the source is to the upper-right of the detector aim. And, since both of the LED's 633 are lit, the polar angle is large, such as greater than 30 degrees. Also, whenever the detector is aligned with the source, a special indicator 634 becomes illuminated, preferably with a different color from the other LED's 631 and 632. Alternatively, all of the LED's 631 and 632 may be flashed brightly whenever the detector is aimed at the source, thereby indicating when the source is located. As a further option, the display 630 could comprise just one circle of indicators 631, but they may be flashed or otherwise modulated according to the polar angle. For example the one LED corresponding to the azimuthal angle could be flashed rapidly if the polar angle is small, and slowly if the polar angle is large, thereby informing the operator of both the azimuthal angle and the (approximate) polar angle simultaneously.

Figure 6B:
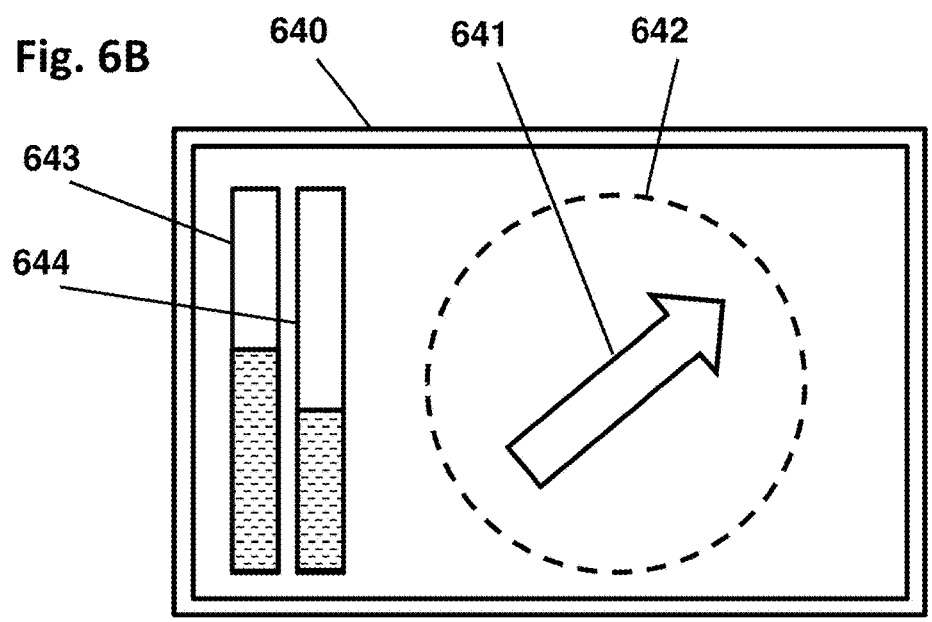
FIG. 6B is a sketch of the inventive screen display including an arrow icon.

FIG. 6B is a sketch of a flat-screen display 640 of the type found on mobile phones, showing a directional icon comprising an arrow 641 which is rotatable, thereby indicating the direction of the source (not shown). Also shown in dash is a bright distinctive icon 642 that is activated in place of the arrow 641 whenever the detector is aimed at the source. The display 640 also includes two ratemeter indicators 643 and 644, showing the highest scintillator counting rate and the central detector counting rate respectively. The display 640 would preferably switch to a "waiting" icon (not shown) during the integration time, to show that the scintillator counts are being accumulated and that the system is not yet able to calculate an azimuthal angle. Then, if no source is present, a non-directional "clear" icon (not shown) could be displayed, thereby indicating to the operator that there is no source present.

Figure 7A:
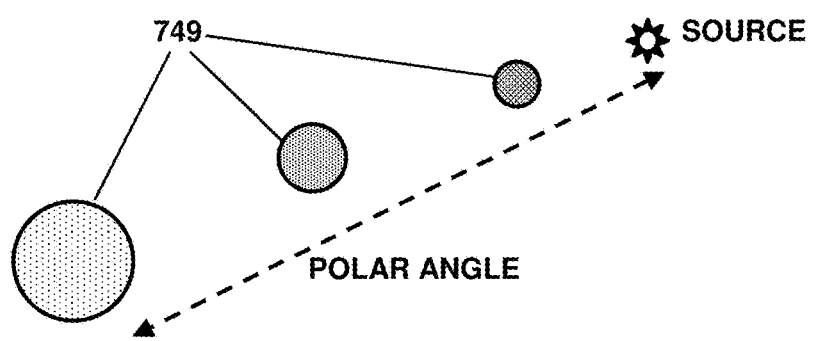
FIG. 7A is a sketch of the inventive light beam modulated according to the polar angle of the source.

FIG. 7A shows a light beam spot 749 configured to be modulated according to the calculated polar angle of the source. When the aim is far from the source, the beam is spread out and the spot 749 is wide. As the detector is rotated closer into alignment with the source, the beam would be more sharply focused, thereby indicating to the operator that the aim is getting closer to the source location. This would assist the operator in finding the source.

Figure 7B:
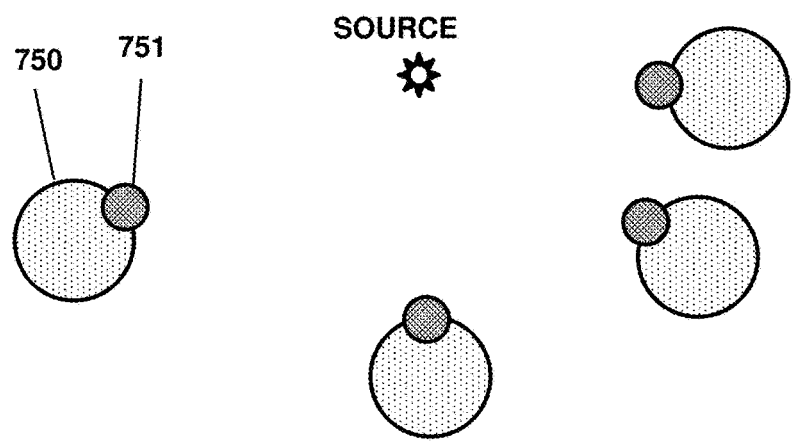
FIG. 7B is a sketch of the inventive light beam modulated according to the azimuthal angle of the source.

FIG. 7B shows an alternative configuration comprising two beams making an asymmetric beam spot. Here a larger fainter portion 750 is combined with a smaller brighter portion 751 to form a directional pattern. In particular, the combined spot is configured to point at the source according to the calculated azimuthal angle. Four different detector orientations are shown at different azimuthal angles around the source position. In an embodiment, the two spot portions 750 and 751 could be generated by two separate light sources (not shown) that are rotated mechanically about an axis according to the azimuthal angle. Or, to avoid the complexity of a mechanical rotation, the system could have a central bright spot beam plus four off-axis beams that form a cloverleaf pattern. Then the larger portion 750 could be produced by one of the four (or more) non-rotating emitters while the smaller, brighter beam 751 could be produced by an axial laser for example. The asymmetric shape, pointing in the azimuthal direction, would then be generated by powering the bright central beam 751 and only one of the peripheral beams 750, to indicate that the source is left or right or up or down relative to the current aim point. To indicate an intermediate angle, two of the peripheral spots 750 could be powered at once, but at different intensities, along with the bright small spot 751. The advantage is simplicity and lower cost since flashlights are cheaper than mechanical rotators.

Figure 8:
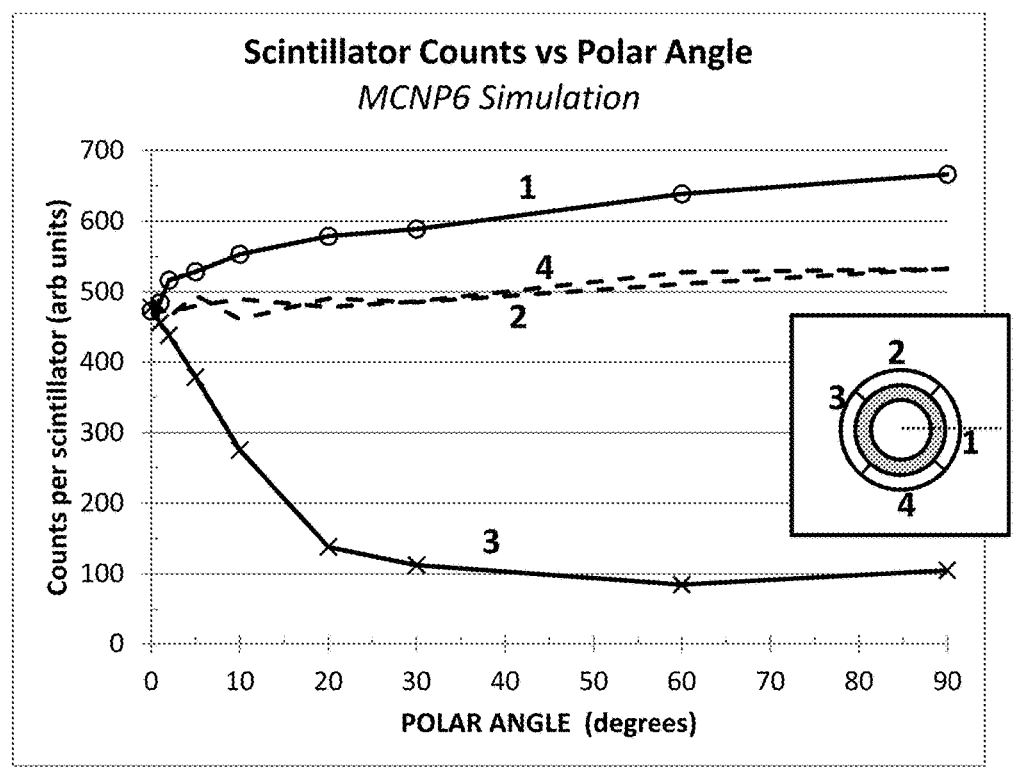
FIG. 8 is a graph showing results of an MCNP6 simulation of the detector of FIG. 4, versus source position.

FIG. 8 is a graph showing results of a simulation using the code MCNP6. Here a 2 MeV gamma ray source was moved to various positions on the horizontal axis while the detector was held fixed pointing at zero degrees and horizontal. The detector was modeled on that of FIG. 1 or FIG. 4. The scintillators were arcurate plastic PVT scintillators 25 mm thick, and 75 mm long in the axial direction. The shield was lead, with a radial thickness of 20 mm, an outer diameter of 90 mm, and a length of 125 mm. There were no scintillator back-flanges. The inset shows the configuration, with the scintillators numbered 1-4 as shown. The dotted line in the inset shows the path that the source traveled in the scan, passing from zero degrees to 90 degrees relative to the detector axis.

The graph shows the counting rate of scintillator 1, plotted as a solid curve with circles, while the horizontal axis shows the polar angle, or net angular displacement, between the source and the detector axis. Also, the counting rate for scintillator 3 is shown as a solid curve with X data points. The other two scintillators, 2 and 4, are shown as dashed curves. As expected, scintillator 1 directly faced the source and thus exhibited the highest counting rate, while the opposite scintillator 3 had the lowest counting rate. The other two scintillators, 2 and 4, had a nearly constant counting rates, since they were positioned orthogonally to the gamma directions. When the detector was pointed substantially directly at the source (polar angle equals zero degrees), all four counting rates were equal, as expected by symmetry. Using this equal-rates criterion alone, the invention found the source location correctly in this simulation, with an error of less than one degree.

Figure 9:
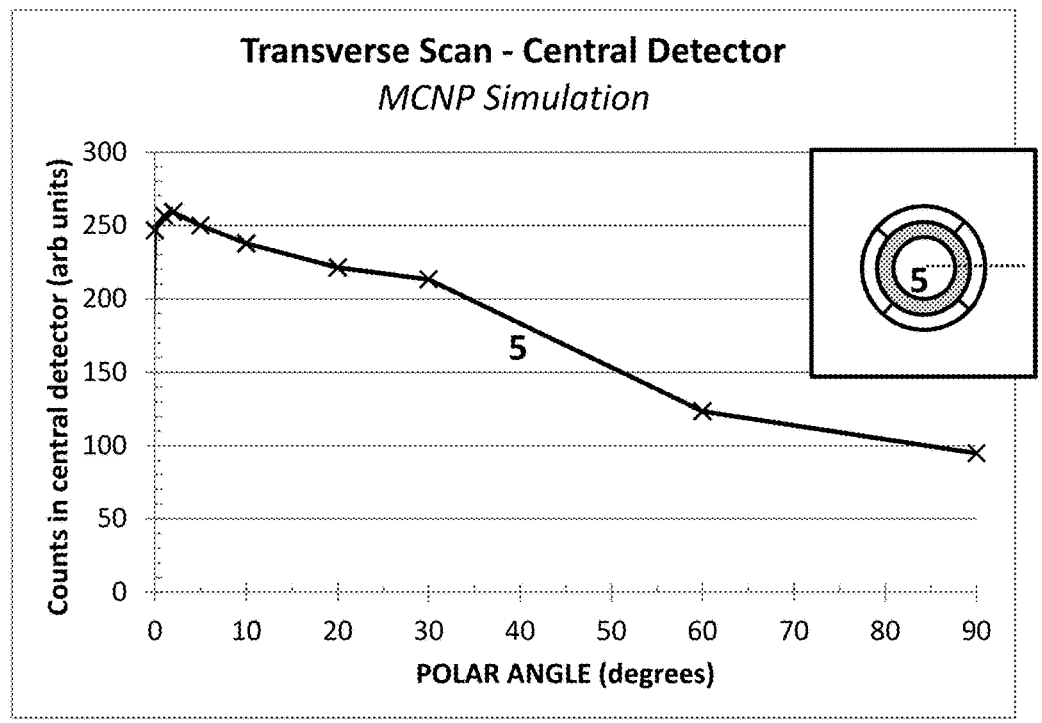
FIG. 9 is a graph showing simulated detection results for the central detector in the configuration of FIG. 4 versus source position.

FIG. 9 is a graph showing the counting rate of the central detector, labeled 5 in the inset, for a simulated scan similar to that of FIG. 8. Again the detector axis is at zero degrees and the source is moved horizontally to 90 degrees. Here the shield inner radius and the central detector outer radius are both 25 mm, the longitudinal thickness of the central detector is 10 mm, and the central detector is recessed by 35 mm from the distal end of the shield. That recessed position provides a particularly advantageous angular response, which enables an accurate determination of the polar angle.

Figure 10:
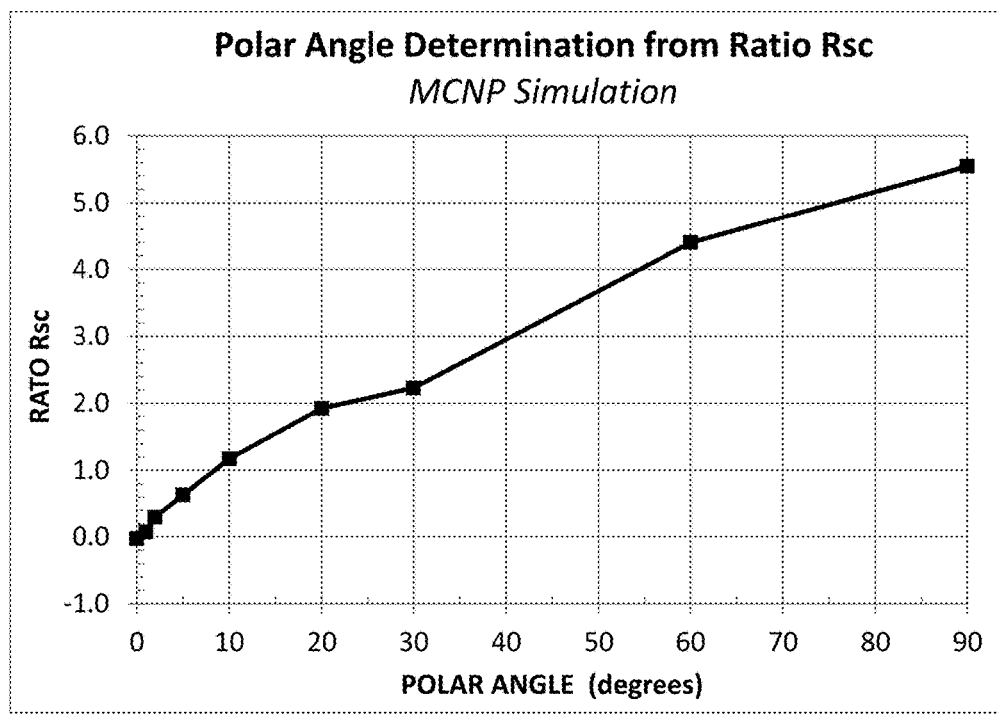
FIG. 10 is a graph showing how the polar angle can be determined using the ratio of the scintillator signals to the central detector signals.

FIG. 10 is a graph showing how the central detector can be used to determine the polar angle of the source. The graph shows Rsc, the ratio of the scintillator differential rate divided by the central detector rate. In the example, Rs is equal to the highest-differential scintillator plus one-half the next-highest differential, while Rc is equal to the central detector counting rate, and Rsc=Rs/Rc. This method provides a nearly uniform scintillator signal regardless of the azimuthal angle of the source and independent of the source intensity. For example, if the azimuthal angle is zero degrees, then scintillator 1 is facing the source, and then the highest differential would be scintillator 1 minus scintillator 3. The other scintillators, 2 and 4, have essentially zero differentials because they are positioned orthogonal to the source. Thus Rs would be essentially equal to the differential of scintillator 1 alone plus a negligible contribution from whichever neighbor happens to have a slight counting excess. If, on the other hand, the source is positioned with an azimuthal angle of 50 degrees, then it would expose scintillator 2 and scintillator 1 about equally, but with 2 being slightly higher. Then Rs would equal the scintillator 2 differential, plus one-half of the scintillator 1 differential. In this way Rs accounts for the azimuthal variation in exposure of each scintillator, but is independent of the azimuthal angle to high accuracy. The central detector rate Rc is also linear in the source intensity and is also azimuthal-independent since it is mounted exactly on the detector axis. Then the ratio Rsc accentuates the different polar angle response functions of the scintillators versus the central detector. The result is the function plotted in FIG. 10, a monotonic correlation between Rsc and the polar angle of the source, independent of the source intensity and independent of the azimuthal angle.

To demonstrate how to use the relationship between the counting rates to determine the polar angle, a specific example is provided with reference to the graphs; however the actual numbers in the example were obtained directly from the MCNP simulation. In this example, the source is located at an azimuthal angle of zero degrees and a polar angle of 60 degrees. That point corresponds to one of the specific cases modeled in FIGS. 8 and 9. At 60 degrees, scintillator 1 had a counting rate of 639 counts in the integration time, while scintillator 3 had 85 counts. The highest differential corresponds to scintillators 1 minus 3 is thus: 639−85=554 in the units of FIG. 8. The next-highest differential, for scintillator 4 minus 2, is 528−511=17, which is a small value as expected since these two scintillators are orthogonal to the gamma beam. Then, Rs is calculated from the highest plus one-half the second highest differential, or Rs=554+17/2=562.5. At the same polar angle of 60 degrees, the central detector has 123 counts. The ratio then is Rsc=562.5/123=4.57. Reading from FIG. 10, and interpolating linearly between the 60 and 90 degree points, a ratio of Rsc=4.57 corresponds to a polar angle of 62.60 degrees. This is close to the actual value of 60 degrees. Thus the polar angle has been determined to about 4% on the first measurement.

The detector is then rotated in the azimuthal direction by the full 62.60 degrees. After the rotation, the detector is then aimed in a direction only 2.60 degrees away from the source location, but now is on the other side of the detector due to the small overshoot. In other words, scintillator 3 is now slightly facing the source. The scintillator rates are again acquired at the new angle. Again reading from FIG. 8, but this time with a polar angle of 2.60 degrees, the highest differential (which is scintillator 3 minus 1 at this orientation) is obtained by weighted averaging between the 2-degree and 5-degree data points of the graph. Using the raw simulation data, this differential equals 92.8. For the two orthogonal scintillators, the second-highest differential is only 2.32, resulting in Rs=92.8+2.32/2=93.94. For the central detector at 2.60 degrees, the interpolated count rate is 257.1. Thus the ratio is Rsc=93.94/257.1=0.365. From the data of FIG. 10, this value of Rsc corresponds to 2.63 degrees and is directed back toward scintillator 1. Accordingly, the detector is rotated back by 2.63 degrees as indicted, which nearly cancels the 2.60-degree overshoot and places the detector axis only 0.03 degrees from the source. Thus the second rotation places the detector axis substantially in alignment with the true source direction, to within sub-degree precision. As a final check, the alignment can then be verified by checking the scintillator rates at this orientation which, according to the data of FIG. 8, are all substantially equal. To summarize, the inventive method located the source to sub-degree precision, in just two steps, by calculating both the azimuthal and polar angles from the central detector and peripheral scintillator counting rates.

In this example, the inventive procedure was described graphically to clarify the steps involved, but the numbers were derived from the actual simulation data, not by measuring the drawings. Likewise in an actual embodiment, the processor would contain all of the factors necessary to calculate the azimuthal and polar angles automatically based on the observed counting rates in cooperation with previously-obtained laboratory calibrations. To calculate the polar and azimuthal angles, the processor would simply ratio the raw scintillator counting rates and derive the source location from those calibration numbers, without the need for graphs and the like. Typically, sub-degree alignment accuracy is obtained in a single step for polar angles of up to 45 degrees, and in two steps for polar angles between 45 and 90 degrees.

Figure 11:
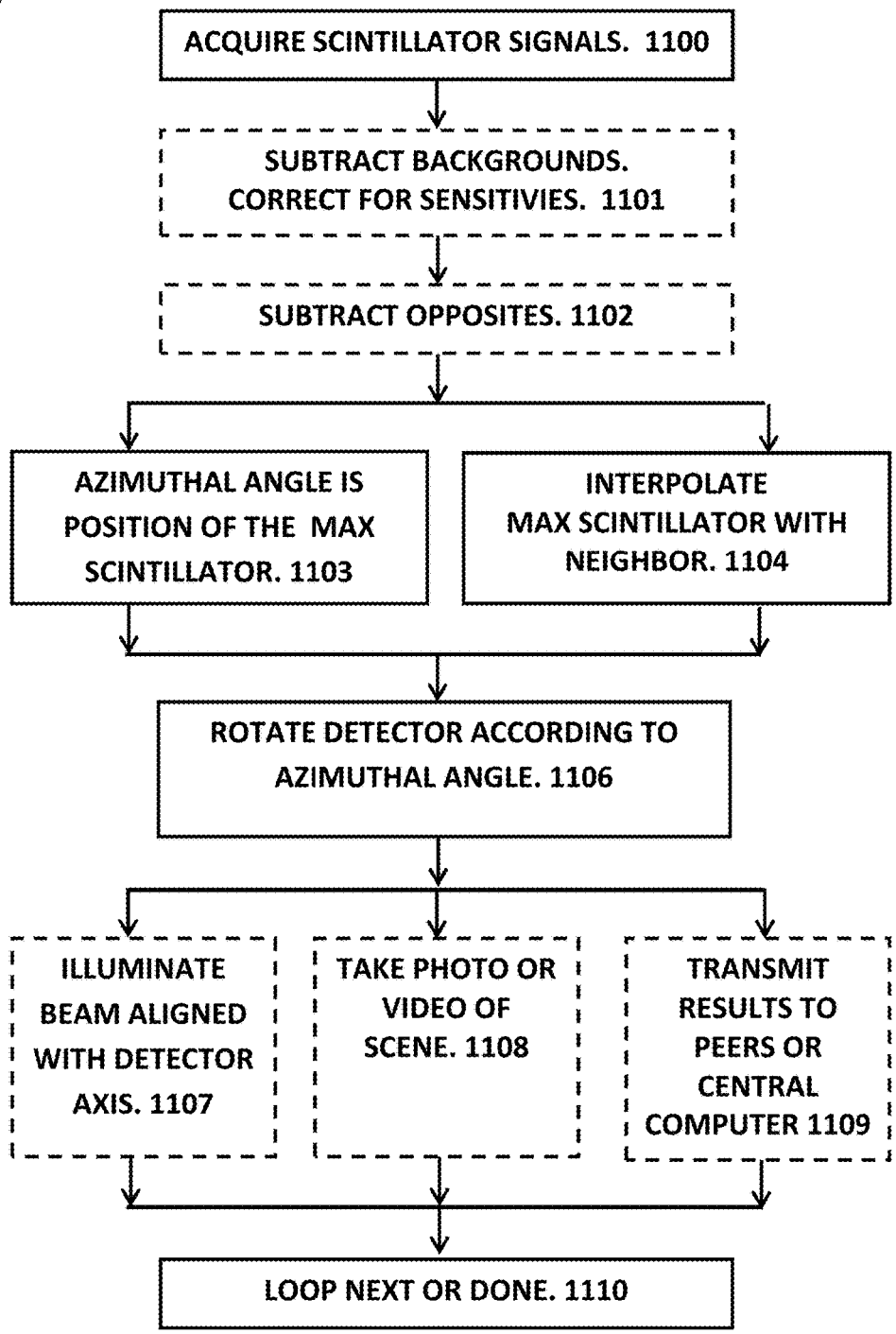
FIG. 11 is a flowchart showing steps of the inventive method for calculating the azimuthal angle from the scintillator data.

FIG. 11 is a flowchart showing how the inventive device may calculate the azimuthal angle from the scintillator signals, as well as activate various accessories. First (1100) the scintillator signals are acquired, which means counting the number of times that each scintillator signal exceeds a voltage or discrimination threshold during an integration time. Additional constraints may also be applied to each signal such as risetime or pulse shape or other signal processing requirements. Veto requirements, or logic-based rejections, may also be applied, such as rejecting any events in which more than one scintillator fires at once. Then (1101) optionally, a previously-determined background rate may be subtracted from each scintillator, thereby calculating a scintillator counting rate above background. Also, the counting rates may be corrected for a previously-calibrated sensitivity or efficiency of each scintillator. Then (1102), a counting rate differential may be calculated for each scintillator, by subtracting the counting rate of the diametrically opposite scintillator, thereby emphasizing the signal contrast between scintillators facing the source and those shielded from the source.

Then the azimuthal angle is calculated, typically using one of two methods. The first method (1103) is simply to identify the particular scintillator with the highest counting rate or the highest differential, and set the azimuthal angle equal to the positional angle of the centroid of that scintillator around the detector axis. For example, if the highest-rate scintillator occupies the upper-right quadrant of the detector, then the azimuthal angle would be 45 degrees relative to the horizontal. This method thus indicates which scintillator is most exposed to the source radiation.

A second and more preferred method (1104) is to identify the two scintillators with the highest counting rates or the highest differentials, and then interpolating between the positional angles of those two scintillators. The azimuthal angle then corresponds to the weighted average of the centroids of those two maximum-counting or maximum-differential scintillators around the detector axis.

After finding the azimuthal angle, the detector is rotated (1106) in the direction indicated. Preferably the rotation is sufficiently slow to allow the detector to follow the changing signals. But even if the operator rotates the detector too rapidly or by too large an angle, the detector will soon update the azimuthal angle based on the updated scintillator signals and will display the new direction, thereby enabling the operator to iteratively converge upon the source direction.

After each rotation, a variety of optional actions may be carried out, including indicating the azimuthal angle just determined (1107), or activating a camera to take a photo or video of the scene as viewed by the detector (1108), or transmitting the measurement results or angular determination to peer detectors in a network or to a central computer (1109).

Then (1110) all the steps of the flowchart are repeated, stopping only when the scintillators all count at the same rate thereby indicating that the source has been found, or when the scintillator rates are all consistent with normal backgrounds thereby indicating that no source is present.

Figure 12:
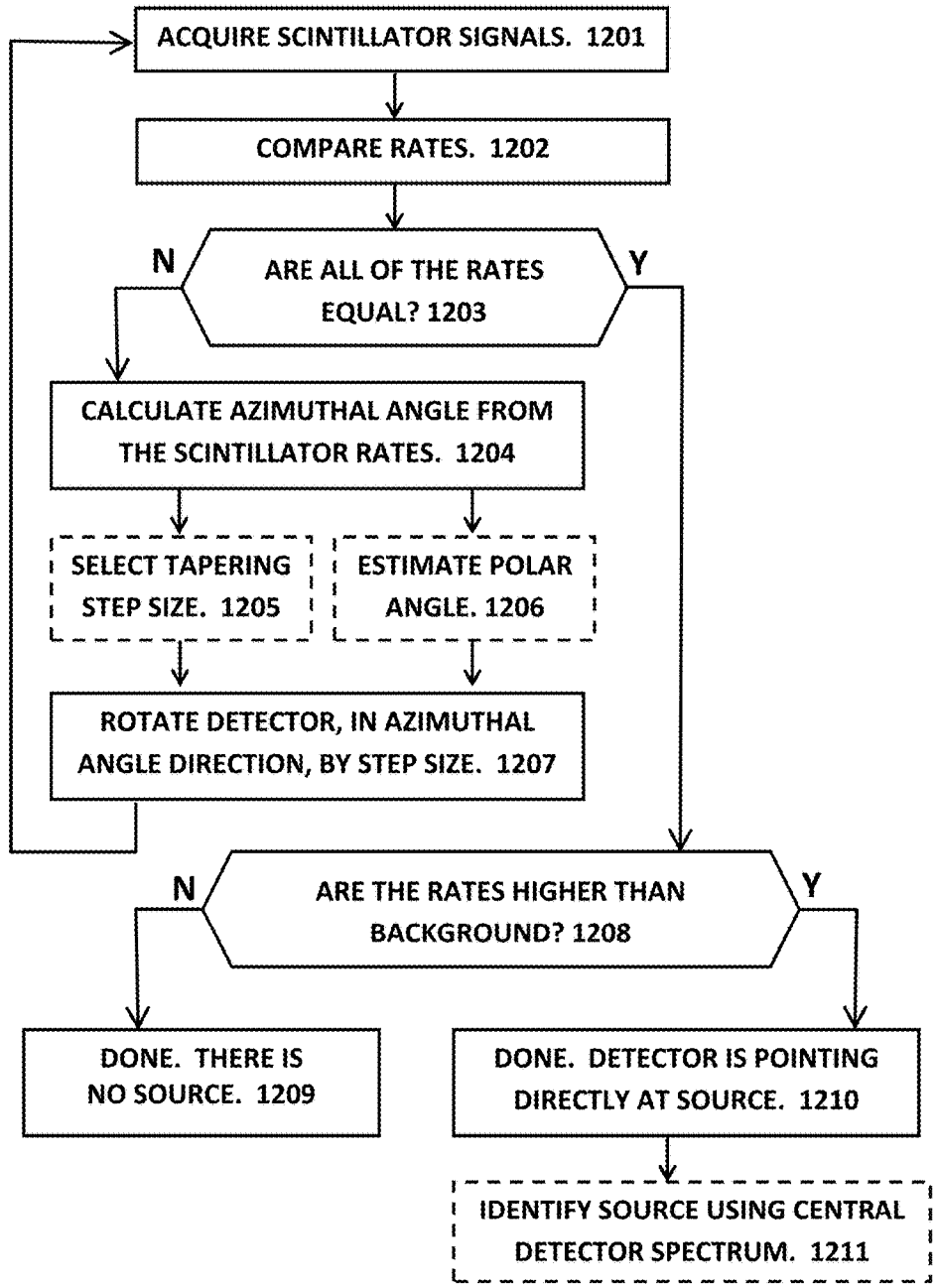
FIG. 12 is a flowchart showing the inventive iterative method to localize the source without calculating a polar angle, using a binary taper for iteratively reorienting the detector.

FIG. 12 is a flowchart showing further details of the inventive method for iteratively rotating the detector to locate the source direction. First (1201) the scintillator signals are acquired at an initially random orientation of the detector, or more preferably centered in the range of travel of the detector. Then, the counting rates of the various scintillators are compared (1202). This comparison may be performed continuously as the data accumulates, or after a certain integration time, or when the total number of counts exceeds a threshold, or when the highest-counting scintillator reaches a threshold value, or according to another criterion. Then (1203) the processor determines whether the counting rates are all substantially equal. Normally they will not be equal, in which case the processor calculates (1204) an azimuthal angle from the scintillator rates. Then, a step size is selected (1205 or 1206), specifying the amount of rotation to apply to the detector. The rotation size may be selected using a predetermined sequence of angular values, or a binary or other geometrical taper for example (1205). Or, the step size can be selected dynamically (1206) by interpolating between two prior measurements at different orientations, or by comparing the scintillator counts with the central detector. Then 1207 the detector is rotated in the direction indicated by the calculated azimuthal angle, by an angle corresponding to the preferred step size. Then the process loops back to 1201 and further data is acquired and the loop is repeated. The loop continues until the scintillator counting rates are all substantially equal at 1203. If they are equal, then the processor checks whether the scintillator rates at the final orientation are higher than the expected background rates (1208). If they are not above background, then (1209) there is no source present and the inspection item is cleared. But if the rates are higher than background, the source is found to be located substantially in alignment with the detector axis (1210). Optionally (1211), a number of responsive actions could be triggered by the processor, upon determining that the detector is aimed directly at the source, such as analyzing spectral data from the central detector to identify the source material. A secondary inspection could be initiated to further explore the radiation source and determine if it is a threat.

Figure 13:
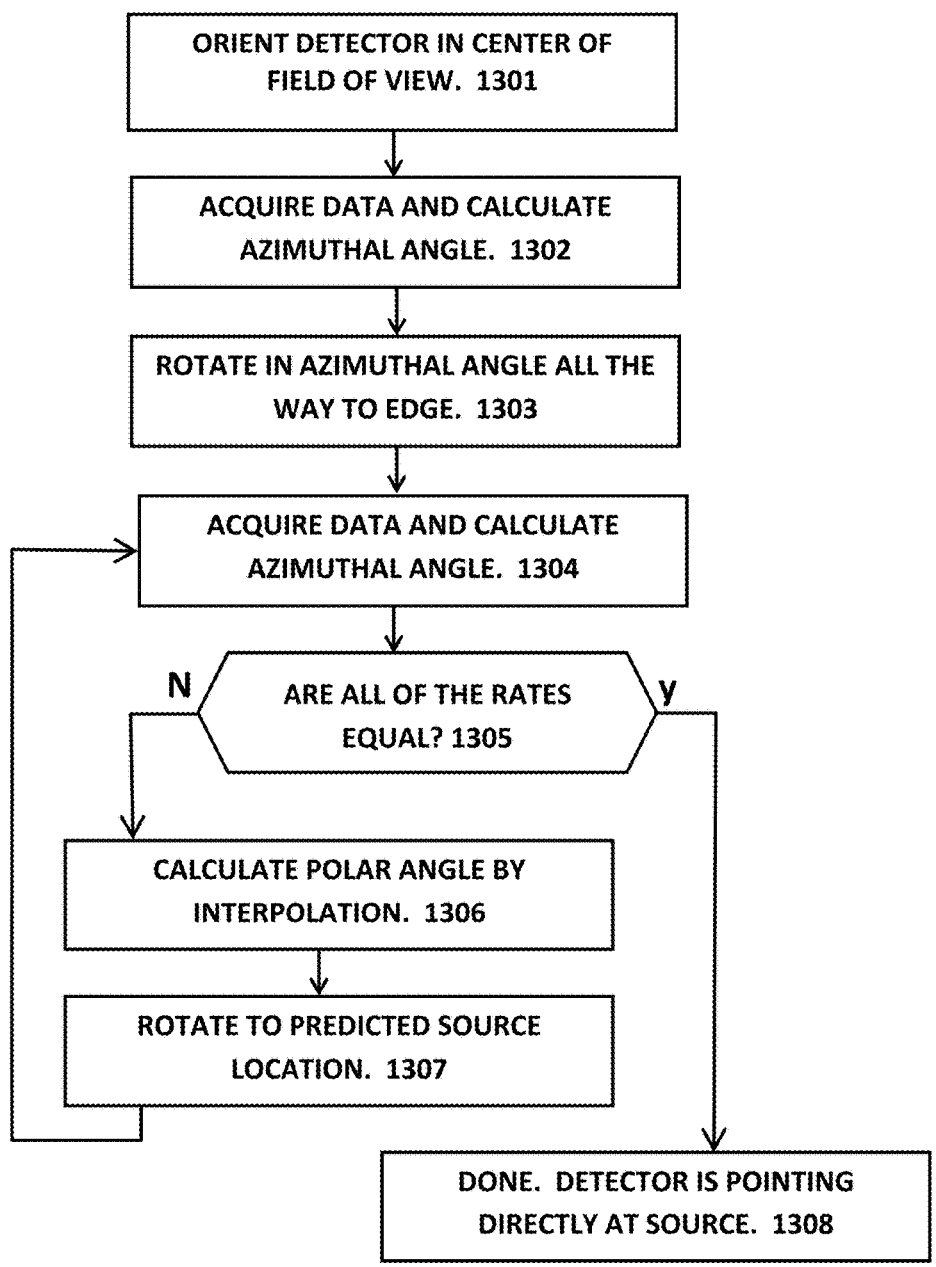
FIG. 13 is a flowchart showing steps of a method to determine both the azimuthal and polar angles using interpolation between successive measurements.

FIG. 13 is a flowchart showing the inventive method to localize the source using interpolation to calculate the polar angle as well as the azimuthal angle of the source. First (1301) the detector is oriented centrally in its field of view or range of travel. Then (1302) the scintillator rates are measured for an integration time, and the azimuthal angle of the source is calculated from that data. Then (1303) the detector is rotated in the direction indicated by the azimuthal angle, all the way to the edge of the field of view (or other limiting range), and a new measurement of the scintillator signals is performed (1304) at that orientation, and a new value for the azimuthal angle is calculated.

Then (1305) the processor compares the rates of the scintillators. If they are all equal, the job is done (1308) and the source is found. Or, if they are substantially equal to the background, the processor would conclude that no source is present.

If the scintillator rates are not all equal, the processor calculates (1306) a polar angle of the source by interpolation between the first and second measurements, which are guaranteed to straddle the source location if the source is anywhere in the field of view. The interpolation may comprise any kind of weighted averaging or analysis involving the two measurement orientations, and their corresponding scintillator signals, in which the source location is anywhere between the first and second measurements. If, on the other hand, the source is actually outside the field of view, then the second azimuthal angle determination would reveal that fact clearly, by pointing farther away from the center. In that case the processor would conclude that there is a source present but it is outside the field of view, and presumably would raise an appropriate alarm.

After calculating the polar angle by interpolation, the detector is then rotated (1307) directly to that predicted source location, according to the azimuthal angle and polar angle just determined. Although the predicted location may not be perfect, it is generally much closer to the true source location than either of the previous measurement orientations. Then (1304) further data are acquired at the new orientation and the loop continues until all the rates are equal and the detector has arrived at the source location.

An advantage of the method of FIG. 13 is rapid convergence, since every measurement, after the first one, is guaranteed to straddle the source location relative to at least one previous orientation. This enables both azimuthal and polar angles to be calculated at each step by interpolation, which allows the detector to be rotated by the right amount needed to reach the predicted source location on every step after the first. The interpolated polar angle results in rapid convergence in just three or four steps typically.

Figure 14:
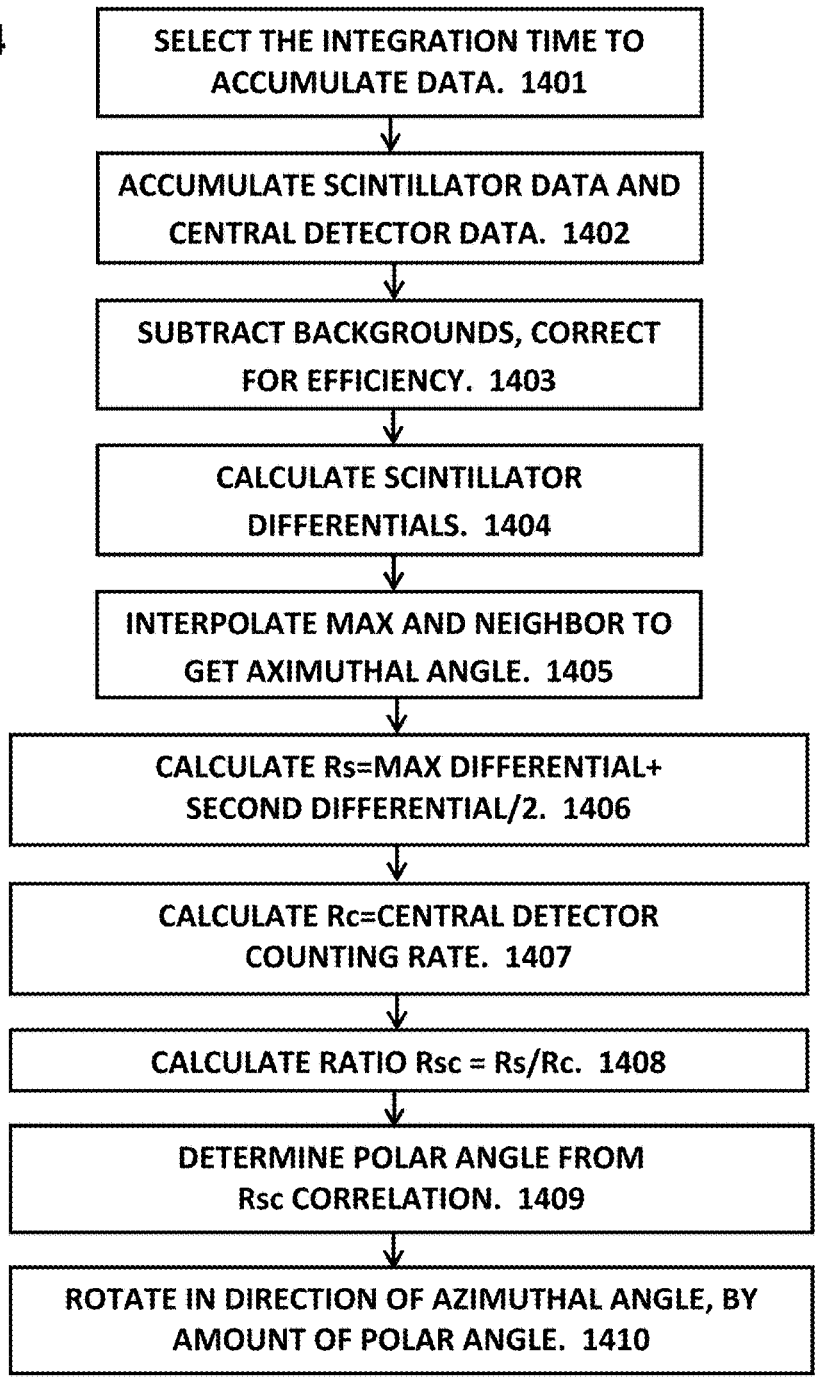
FIG. 14 is a flowchart showing steps of a method for localizing the source by calculating the azimuthal angle from the scintillator array, and a polar angle from the central detector.

FIG. 14 is a flowchart showing steps of the inventive method to calculate the polar angle using the central detector. First 1401 a variable integration time is selected, based on the ambient radiation level for example, or simply a default time interval. Then 1402 the scintillator signals and the central detector signals are accumulated for the integration time. After accounting for backgrounds and efficiency differences among the scintillators (1403), the scintillator differentials are calculated by subtracting the diametrically opposite counting rate from that of each scintillator (1404).

Then the azimuthal angle is calculated 1405 by interpolating between the two highest-differential scintillators.

Then the polar angle is calculated. First 1406 the effective scintillator rate Rs is derived by adding the maximum scintillator differential plus one-half the next-highest differential in the scintillator array. The central detector rate Rc is then 1407 determined from the data, and the ratio Rsc=Rs/Rc is calculated at 1408. This ratio provides a rate-independent, azimuth-independent, value correlating with the polar angle. The polar angle is then determined at 1409 according to Rsc and the previously-calibrated correlation factors of the scintillators. The source location is thus determined, comprising the calculated azimuthal and polar angles. This data may then be communicated to a central computer. Then (1410) the detector is rotated, in the direction of the azimuthal angle, and by an amount of the polar angle, thereby arriving closely at the source direction. If the scintillators indicate that the detector axis is not yet centered on the source, the steps are repeated and the detector is again rotated as indicated. Typically the source is found, to sub-degree precision, in a single step if the initial polar angle is less than about 45 degrees, or in two steps if greater than about 45 degrees.

The inventive detector offers numerous advantages not previously available in any practical prior-art detector. The inventive detector is enabling, in applications ranging from cargo inspection, to walk-through portals, to portable survey meters, to mobile scanners searching for unexpected radiation in an urban environment, and many other critical applications. On a single measurement, the detector indicates the source direction relative to the detector axis. With further data, the detector then localizes the source rapidly and precisely in two dimensions. Or, with a central detector properly configured, the invention can determine both the azimuthal and polar angles at once. High detection efficiency is provided by the scintillator array which substantially surrounds the shield, thereby providing as much detector area to the incoming gamma rays as possible. Since the scintillators are mounted closely proximate to the shield, they reduce mass, eliminate wasted space, and sharpen the signal contrast. The shield is hollow to reduce unnecessary weight while still providing effective attenuation of gammas. Unlike prior-art detectors based on collimation, the inventive shield does not block gammas from reaching the detector from any angle, since at least one scintillator is fully exposed to the source regardless of the source location, resulting in high and unimpeded detection efficiency. Unlike prior-art collimated detectors, the inventive shield only prevents gammas from passing all the way through the detector, and does not prevent gammas from reaching the first scintillator facing the source. Hence the detector has much higher detection efficiency than any conventionally-collimated detector. The inventive detector also provides very high angular precision by indicating when the scintillators have about the same counting rate. The inventive detector is compact, self-contained, rugged, reliable, and cheap.

Advanced radiation detection systems like that disclosed herein, will be needed in the coming decades to protect innocent people from the threat of nuclear and radiological terrorism.

The embodiments and examples provided herein illustrate the principles of the invention and its practical application, thereby enabling one of ordinary skill in the art to best utilize the invention. Many other variations and modifications and other uses will become apparent to those skilled in the art, without departing from the scope of the invention, which is to be defined by the appended claims.

What is claimed is:

1. A device comprising:
a shield;
an array of scintillators;
a processor; and
a detector axis;
wherein:
the shield comprises material that substantially blocks or attenuates gamma rays; the shield comprises a hollow, substantially tubular form having an exterior circumferential surface;
the shield has an axis of symmetry comprising the detector axis; the scintillator array comprises at least four scintillators mounted in close proximity to the exterior circumferential surface of the shield;
the scintillator array comprises a substantially gapless tubular assembly that substantially surrounds the exterior circumferential surface of the shield;
each scintillator is closely in contact with neighboring scintillators; and
the processor is configured to determine, based on signals from the scintillators, an azimuthal angle of a gamma ray source relative to the detector axis.

2. The device of claim 1, wherein the processor is configured to determine, based on the signals from the scintillators, a polar angle of the gamma ray source relative to the detector axis.

3. The device of claim 1, wherein the processor is configured to activate, when all of the scintillators have substantially equal counting rates, an indicator indicating that the detector axis is substantially aligned with the gamma ray source.

4. The device of claim 1, wherein each scintillator comprises an arcurate shape which substantially matches the exterior circumferential surface of the shield.

5. The device of claim 1, wherein the scintillators comprise substantially flat plates mounted symmetrically around the exterior circumferential surface of the shield.

6. The device of claim 1, wherein:
the device includes a front face comprising a plane perpendicular to the detector axis;
the scintillator array is bounded by the front face; and
the shield protrudes distally beyond the front face.

7. The device of claim 1, wherein:
a scintillator back-flange, comprising scintillator material, is mounted at the rearmost region of each scintillator; and
each back-flange extends radially beyond the exterior circumferential surface of the scintillator array.

8. The device of claim 1, which further includes a central detector positioned within the shield and configured to detect gamma rays.

9. The device of claim 8, wherein the processor is further configured to determine, by comparing signals from the central detector to signals from the scintillators, a polar angle of the gamma ray source relative to the detector axis.

10. The device of claim 1, which further includes an indicator comprising a circular array of luminous components that indicate the azimuthal angle of the gamma ray source relative to the detector axis.

11. The device of claim 1, wherein the device further includes a flat-screen display configured to show a rotatable icon that indicates both the azimuthal angle and the polar angle of the gamma ray source relative to the detector axis.

12. The device of claim 1, wherein the processor is further configured to activate a haptic or acoustical indicator when the detector axis is substantially aligned with the gamma ray source.

13. The device of claim 1, wherein:
the device includes a multi-axis accelerometer and an electronic compass; and
the processor is configured to determine, based on signals from the accelerometer and the compass, an orientation of the detector axis.

14. The device of claim 1, wherein:
the device is affixed to a structure;
the device includes at least two substantially orthogonal electronic angular encoders; and
the processor is configured to determine, based on signals from the angular encoders, an orientation of the detector axis.

15. The device of claim 1, wherein the processor is configured to activate a camera when the detector axis is substantially aligned with the gamma ray source.

16. The device of claim 1, wherein:
the device includes a light beam;
the processor is configured to determine a polar angle of the gamma ray source relative to the detector axis; and
the processor is configured to vary a property of the light beam according to the polar angle of the gamma ray source relative to the detector axis.

17. The device of claim 1, wherein:
the device includes a wireless communicator;
the device includes a GPS receiver;
the processor is configured to transmit, when the detector axis is substantially aligned with the gamma ray source, information about the detector position and the detector orientation.

18. The device of claim 1, wherein the processor is configured to accumulate the scintillator signals for a variable integration time.

19. The device of claim 18, which further includes a manually operated control that adjusts the variable integration time.

20. The device of claim 18, wherein the processor is further configured to adjust the variable integration time according to the scintillator signals.

* * * * *